(12) United States Patent
Thompson et al.

(10) Patent No.: US 7,119,251 B2
(45) Date of Patent: Oct. 10, 2006

(54) BASAL ENDOSPERM TRANSFER CELL LAYER (BETL) SPECIFIC GENES

(75) Inventors: Richard D. Thompson, Cologne (DE); Francesco Salamini, Cologne (DE); Gregorio Hueros, Madrid (ES)

(73) Assignee: Max-Planck-Gesellschaft zur Forderung der Wissenchaften e.V., Berlin (DE)

( * ) Notice: Subject to any disclaimer, the term of this patent is extended or adjusted under 35 U.S.C. 154(b) by 511 days.

(21) Appl. No.: 10/422,365

(22) Filed: Apr. 23, 2003

(65) Prior Publication Data

US 2004/0003427 A1 Jan. 1, 2004

Related U.S. Application Data

(62) Division of application No. 09/647,376, filed as application No. PCT/EP99/02063 on Mar. 26, 1999.

(30) Foreign Application Priority Data

Mar. 27, 1998 (EP) .................................. 98105628

(51) Int. Cl.
| | |
|---|---|
| C12N 15/29 | (2006.01) |
| C12N 15/82 | (2006.01) |
| C12N 15/87 | (2006.01) |
| C12N 5/04 | (2006.01) |
| A01H 1/00 | (2006.01) |

(52) U.S. Cl. .................. 800/278; 536/24.1; 435/320.1; 435/410; 435/419; 800/290; 800/287; 800/320.1

(58) Field of Classification Search .............. 536/24.1; 800/278, 298, 290, 287, 320.1; 435/320.1, 435/410, 419, 468
See application file for complete search history.

(56) References Cited

U.S. PATENT DOCUMENTS 6,071,700 A 6/2000 He et al.

FOREIGN PATENT DOCUMENTS

| WO | WO 97/04116 | * | 2/1997 |
|---|---|---|---|
| WO | WO 97 04116 A | | 2/1997 |
| WO | WO 98 08961 A | | 3/1998 |

OTHER PUBLICATIONS

Kagaya et al (1995, Mol. Gen. Genet. 248 :668-674).*
Benfey et al (1990, Science 250:959-966).*
Benfey et al (1989, EMBO J, 8(8):2195-2202).*
Oommenn et al (1994, The Plant Cell 6:1789-1803).*
Merriam Webster Online Dictionary. 2005, www.m-w.com/home.html.*
Finnegan and McElroy, 1994, Bio/Technology 12:883-888.
Eshed et al., 2001, Current Biology 11:1251-1260.
Stone et al., 2001, PNAS vol. 98 No. 20:1180-1181.
Fourgoux-Nicol et al. 1999, Plant Molecular Biology 40:857-872.
Artavanis-Tsakonas et al., Nov. 12, 1992; Accession No. AAQ30992; N. Geneseq database.
Hueros et al., Molecular Characterization of BET1, a Gene Expressed in the Endosperm Transfer Cells of Maize, 1995, The Plant Cell, vol. 7, pp. 747-757.
Charlton, W.L. et al., Endosperm development in zea-mays—implication of gametic imprinting and paternal excess in regulation of transfer layer development, Development, vol. 121, No. 9, Sep. 1995, pp. 3089-3097.
Chen, Y-C. and Chourey, P.S., Spatial and temporal expression of the two sucrose synthase genes in maize, Theoretical and Applied Genetics, vol. 78, No. 4, 1989, pp. 553-559.

* cited by examiner

*Primary Examiner*—Stuart F. Baum
(74) *Attorney, Agent, or Firm*—Stewart, Kolasch & Birch, LLP

(57) ABSTRACT

Described are nucleic acid molecules encoding basal endosperm transfer cell layer (BETL) specific proteins as well as regulatory sequences which naturally regulate the expression of such nucleic acid molecules. Vectors comprising said nucleic acid molecules, wherein the nucleic acid molecules are operatively linked to regulatory elements allowing expression in prokaryotic and/or eukaryotic host cells as well as proteins encoded by said nucleic acid molecules, antibodies to said proteins and methods for their production are provided. Described are also recombinant DNA molecules and vectors comprising said regulatory sequences as well as host cells transformed therewith. Furthermore, kits and diagnostic compositions comprising the aforementioned nucleic acid molecules, proteins, antibodies, regulatory sequences, recombinant DNA molecules and vectors as well as antibodies are provided. Also provided are methods for the identification of compounds being capable of activating or inhibiting the expression of BETL specific genes. Furthermore, transgenic plant cells, plant tissue and plants containing the above-described nucleic acid molecules, regulatory sequences, recombinant DNA molecules and vectors as well as the use of the aforementioned nucleic acid molecules, regulatory sequences, recombinant DNA molecules, vectors, proteins, antibodies, peptides and/or compounds identified by a method of the invention in plant cell and tissue culture, plant breeding and/or agriculture are described.

Figure 1:
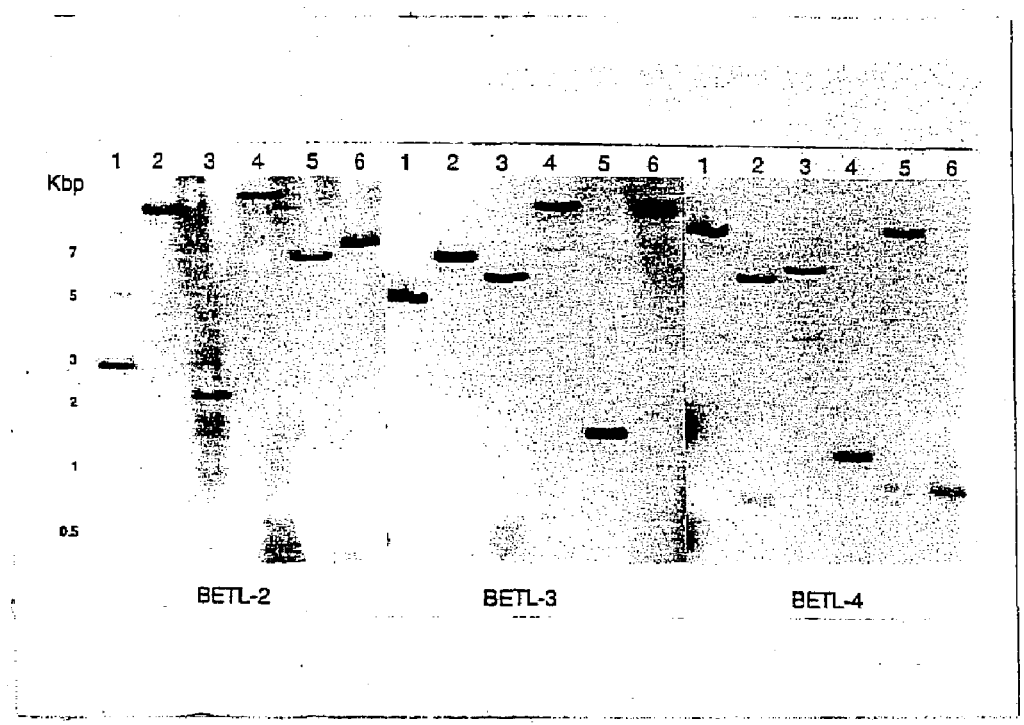

19 Claims, 14 Drawing Sheets sense probe antisense probe

GUS activity during tobacco seed development

Figure 13

```
BETL1 (SEQ ID NO: 7)    1 ..............................................
BETL4 (SEQ ID NO: 10)   1 ..............................................
BETL2 (SEQ ID NO: 8)    1 AATTCCCATTTGTTACCGATGCCTGTTACTAGTTTCATATGATGGAAAAC
BETL3 (SEQ ID NO: 9)    1 ..............................................

BETL1 (SEQ ID NO: 7)    1 ..............................................
BETL4 (SEQ ID NO: 10)   1 ..............................................
BETL2 (SEQ ID NO: 8)   51 TAGGAGCAACAGACTTCTCCAACGTACGTGTTAATTTTCTAATTGATTCT
BETL3 (SEQ ID NO: 9)    1 ..............................................

BETL1 (SEQ ID NO: 7)    1 ..............................................
BETL4 (SEQ ID NO: 10)   1 ..............................................
BETL2 (SEQ ID NO: 8)  101 TCTAACCCTCCAATTTGTTGTTTCATTTGATTCTGATGATGATCTACATA
BETL3 (SEQ ID NO: 9)    1 ..............................................

BETL1 (SEQ ID NO: 7)    1 ..............................................
BETL4 (SEQ ID NO: 10)   1 ..............................................
BETL2 (SEQ ID NO: 8)  151 CTGTTTAATAGATTGGATGTCGTCGGGTGTACTTACGTTAGGGACTTGAA
BETL3 (SEQ ID NO: 9)    1 ..............................................

BETL1 (SEQ ID NO: 7)    1 ..............................................
BETL4 (SEQ ID NO: 10)   1 ..............................................
BETL2 (SEQ ID NO: 8)  201 GCGGAGATAGAAGAGATGTGATGTTGGTCTCTCCATGTTTGACAACTTTC
BETL3 (SEQ ID NO: 9)    1 ..............................................

BETL1 (SEQ ID NO: 7)    1 ..............................................
BETL4 (SEQ ID NO: 10)   1 ..............................................
BETL2 (SEQ ID NO: 8)  251 TGGTGGTGATCCACCGTGTATTGTGATAAGAATTTCTCCTTTGCTTGACA
BETL3 (SEQ ID NO: 9)    1 ..............................................

BETL1 (SEQ ID NO: 7)    1 ..............................................
BETL4 (SEQ ID NO: 10)   1 ..............................................
BETL2 (SEQ ID NO: 8)  301 CATGTAGTCCTCGTATTGCTGTTGCTCATCGGCCGTTAGTCTTTCAACAG
BETL3 (SEQ ID NO: 9)    1 ..............................................

BETL1 (SEQ ID NO: 7)    1 ..............................................
BETL4 (SEQ ID NO: 10)   1 ..............................................
BETL2 (SEQ ID NO: 8)  351 CCGGCTTCAGGATATTGTCCGGGGGAGATATCAGTGTGATCTTTAGAACC
BETL3 (SEQ ID NO: 9)    1 ..............................................

BETL1 (SEQ ID NO: 7)    1 ..............................................
BETL4 (SEQ ID NO: 10)   1 ..............................................
```

Figure 13 (continued)

```
BETL2 (SEQ ID NO: 8)    401 GGGCCATTTGAGGGGCCTGATTTTTAGTAGATCAAGACACCTGTCCCAGC
BETL3 (SEQ ID NO: 9)      1 ..................................................

BETL1 (SEQ ID NO: 7)      1 ..............................................CAC
BETL4 (SEQ ID NO: 10)     1 ..................................................
BETL2 (SEQ ID NO: 8)    451 GGAGTCGCCAAAAAGAGTGTTGGCGCCGGTTCGGGCACCAATCACTGCAT
BETL3 (SEQ ID NO: 9)      1 ..................................................

BETL1 (SEQ ID NO: 7)      4 CAGGATCAGGAACCAGGAATCTGATACCAATTGTAATAGAACCATGGA.A
BETL4 (SEQ ID NO: 10)     1 ..................................................
BETL2 (SEQ ID NO: 8)    501 TGAGAACCTGCCGGCGGTGCTCTCTGCACAGGCGCGGACGGTTCACGGCTA
BETL3 (SEQ ID NO: 9)      1 ..................................................

BETL1 (SEQ ID NO: 7)     53 CAGGTAACAGAGCCGATGAACACA...AAGACATGATTTGGATCACGAGC
BETL4 (SEQ ID NO: 10)     1 ..................................................
BETL2 (SEQ ID NO: 8)    551 GAGGCCAGACGGTCCGCGACCTGGTGCAGGGCTCGAGTTCCCTGCCTAAC
BETL3 (SEQ ID NO: 9)      1 ..................................................

BETL1 (SEQ ID NO: 7)    100 ACGGCTCCTGGTACCGTCCACCTCTGACGAAGTATCAAATTATCACTGGA
BETL4 (SEQ ID NO: 10)     1 ..................................................
BETL2 (SEQ ID NO: 8)    601 GAGACGGATGGTCGGCGCCTAGGGGCCGGACGGTACGCGCGTGCACAGGG
BETL3 (SEQ ID NO: 9)      1 ..................................................

BETL1 (SEQ ID NO: 7)    150 ATTCATGATTCAGGTTACAGAGGAAGAGCCCTCCCTTTCCGAACGCAGTC
BETL4 (SEQ ID NO: 10)     1 ...................................................
BETL2 (SEQ ID NO: 8)    651 GCGGCGGAGTTTGTCGGCCGCCGTCTGAATCTCGCTCTGGGGAGGGACCCC
BETL3 (SEQ ID NO: 9)      1 ..................................................

BETL1 (SEQ ID NO: 7)    200 GGCCTCAACTTATGCCCCAAGCCGCGCTTGCCGATTCATAAAGTCCTTTT
BETL4 (SEQ ID NO: 10)     1 ..................................................
BETL2 (SEQ ID NO: 8)    701 GCCAGGAAAGAGAGATCCTAGGCTTCGTCTAGGGTCGGCAG...GCCACC
BETL3 (SEQ ID NO: 9)      1 ..................................................

BETL1 (SEQ ID NO: 7)    250 CTTTATACCACATGCCAAAACAAAAA.GAAAACACTAAAACACTCATTGG
BETL4 (SEQ ID NO: 10)     1 ..................................................
BETL2 (SEQ ID NO: 8)    748 CTAGACACCTCTAATCAACGTAGAGCCGAAGAGAAGCGAAGAATTTGGCG
BETL3 (SEQ ID NO: 9)      1 ..................................................

BETL1 (SEQ ID NO: 7)    299 GTCCAATCTGGCCCATGGAC.GCGAGAGTTGGGCTTCACTTGAC....AT
BETL4 (SEQ ID NO: 10)     1 ..................................................
BETL2 (SEQ ID NO: 8)    798 GTAGGGAAAGGCTAATCTAGAGCTAAACTAGAACTACTCCTAATGCATAA
BETL3 (SEQ ID NO: 9)     12 ATTTGACAATATTTATGATTAGAGATATTTCCTCCTTAATAATTGC...GT
```

Figure 13 (continued)

```
BETL1 (SEQ ID NO: 7)   344 CGAACCGTCCTAGTAGCCATGGTTCCTTCCGGCCTTCTGTTGATTTGCTT
BETL4 (SEQ ID NO: 10)    1 ..................................................
BETL2 (SEQ ID NO: 8)   848 GTAAAACGAGAATAGACACGATT..TGATCGATTGTTGGGGGTTCAATC
BETL3 (SEQ ID NO: 9)    60 GGGAATCGACGTATGGCCATGAAC.....TCAAGGTATGTACAATCCTGA

BETL1 (SEQ ID NO: 7)   394 CGGTGTCATCACACATCGTTGGACCACATTCCAGACGTCCATACACCGAG
BETL4 (SEQ ID NO: 10)    1 ..................................................
BETL2 (SEQ ID NO: 8)   896 GGCCGTAGCCCTTCATCTAT..ATAAAGGGGGAGGTCTGGATCCGCTACA
BETL3 (SEQ ID NO: 9)   105 GACTC...CCGTTCAGTTTT...CAAAAATACA......ATAAACGGTT

BETL1 (SEQ ID NO: 7)   444 TATACAGGAAAGAGAGACAACGGGGTGAACCGTTGACACGGCCTGGAAAC
BETL4 (SEQ ID NO: 10)    1 ..................................................
BETL2 (SEQ ID NO: 8)   944 AGTTGTTTCCGAGCTAATCCCGTAATTTTAGGTAACAAATCGCGCGACA
BETL3 (SEQ ID NO: 9)   142 AAGAGACTGCATATACAACCCTGAGATTCTGGATCATAAA...TGTAACT

BETL1 (SEQ ID NO: 7)   494 AATGGTGGCGGCTGGAAACAACAGCAGCCATTGTGACAACGACTAAATAG
BETL4 (SEQ ID NO: 10)    1 ...........................TTTAAAAAAAACGAA.TCT
BETL2 (SEQ ID NO: 8)   994 AA..CTCGGAACCTTAACTGACTCTAGCCGACGTAA.ATTATCGAA.TTT
BETL3 (SEQ ID NO: 9)   189 AA..GAGACAACATGTATGGACAG......TCGTGA.AGAAACGTGCTAT

BETL1 (SEQ ID NO: 7)   544 GGTTGAAC.CGCCTTTGCCAATGATTTTTTGCCGT.TTACCCTTTGCCG
BETL4 (SEQ ID NO: 10)   19 GGTTGAAG.AGC..TCGATTTTAATTAAAAAGAAGA.ATAAGCTTT....
BETL2 (SEQ ID NO: 8)  1040 CCTTGTAGTATCTGTCCTAAGCAATGAAAATACCTTTATAAGATGG.CAA
BETL3 (SEQ ID NO: 9)   230 TCGCGAAGAACCCGTCGCTTGTATTTTTTTCACC....TAGCCTCT....

BETL1 (SEQ ID NO: 7)   592 GGTGTGACACTCTGCAAAAGGT.T.TACTGTCTGTATTT.CTGGCTTTGC
BETL4 (SEQ ID NO: 10)   61 GTTAAAACAGACTTCAAGACCT.AATAATAAACACAAGA.AGAAGTTACA
BETL2 (SEQ ID NO: 8)  1089 GGACCAACATTGTTCTAGAAAGAAAAATCAGGAAAAGAGAGGGCATTG.
BETL3 (SEQ ID NO: 9)   272 .TAGAGACCCATAGAGAAACCC.TATATTA...CATAGGCTTGTACATGCC

BETL1 (SEQ ID NO: 7)   639 CGAGTGCATG....GGGCACTCGGCAA...AGCATGTGACT..CTGGTAG
BETL4 (SEQ ID NO: 10)  109 TGCATACAAGAGAAGGGCATAGGCAC...AAGAAAAACTACCTAGAAA
BETL2 (SEQ ID NO: 8)  1138 .TATTGCCCGC...GGGAA.CATGCAACCGAGCTAATGATATTCATGAGC
BETL3 (SEQ ID NO: 9)   318 CGAATACATTCCAATGTTACAAATTAATGTTCGTATTTACCATTAAGCAA

BETL1 (SEQ ID NO: 7)   680 TGTCTATGCTATGTAGAC....GCACC.TCCA.AG...CTTAGG.T.ATC
BETL4 (SEQ ID NO: 10)  155 GGTATAGGCTGATCACACAT.GTTCA.TTTC.AGG...CTTGGCT.CTG
BETL2 (SEQ ID NO: 8)  1183 TGTTTGGTTCCATTCAACTAAAGTTTAGTCTG.TGTCACTTCGG...ATG
BETL3 (SEQ ID NO: 9)   368 .GTATATACTTAA.GCACTA..AATCATTGTGCAATTACTTTGAATACTA

BETL1 (SEQ ID NO: 7)   719 .TTTCGT...CTAAGCATTT..ATGCATT.AATG.TCTA.ATATCTTC...
BETL4 (SEQ ID NO: 10)  198 GTTTCGTAGCTATGCCTTTGTATGCATT.AGTGATCTA.CTTGTCTA...
```

Figure 13 (continued)

```
BETL2(SEQ ID NO: 8)   1229 .TTCCAATGATAATTGTGAGTGTTAAAT.ATAGTTTAA.ATATAAAAC.
BETL3(SEQ ID NO: 9)    414 ATATCTAT..TAAATCTGTATCTGGATTTAGTTGTTTAGATACCATCGAA

BETL1(SEQ ID NO: 7)    758 ..TTATTAGATTGCAAAATAATTAGTAGTG.GAAGA.....ACAACCA..
BETL4(SEQ ID NO: 10)   243 ..TAATGACTTTGTAGA.TATTAACATGCC.CATGGTG...TACACGCA..
BETL2(SEQ ID NO: 8)   1275 ..TAATTATACAGATAAGACTAAAGGCGACACAATTTTATTAAACCTAAT
BETL3(SEQ ID NO: 9)    462 ATTAATAGGGTTGTTCATAATGTATTTGAATTAAAAA.ACAATAGCTATT

BETL1(SEQ ID NO: 7)    798 TT...GCAAATATGTTGGTT...GTCTT.TGTATGAC.TAAACCAATATCAT
BETL4(SEQ ID NO: 10)   285 T....GCTTTAATGGACGTG...ATTTTATAGATACC.TGCACCTA.ATGAG
BETL2(SEQ ID NO: 8)   1323 TA..GTTTGTATTTAATTCTCATAGTTGATATAC.TAGATAGGTAGGCA
BETL3(SEQ ID NO: 9)    511 TCGTGCCATAATTAAATTGT.TTGATACGGATGATATCAACAAAGATCTA

BETL1(SEQ ID NO: 7)    842 CATATTATATCAACAA...CAACATA............TCCCAAT....
BETL4(SEQ ID NO: 10)   328 CATATCTGAGAAAGATGTTCATCATAAATG........TTACCAT....
BETL2(SEQ ID NO: 8)   1370 CATAT.ATAGAGAGAT.....AGATA...........TAAATAG....
BETL3(SEQ ID NO: 9)    560 GATAGAAGGTTCGGATATTTTTCACAACTGCAAAATCATTTCACAGCAGA

BETL1(SEQ ID NO: 7)    872 ATCTATATCCATAACTATATCTATATGTAAAATTTCT.ATATCTCTATCT
BETL4(SEQ ID NO: 10)   365 ATCTTCACCCCCCCCACAGACACACACACACACGCATATCCATATCG
BETL2(SEQ ID NO: 8)   1397 ATATAAATAAGTAGATAGATAGATAGATAGATAGATAGATAGATAG
BETL3(SEQ ID NO: 9)    610 ATATCTTCGCATTATTATA.AGACGAGAACATATTTTTGTAGA.AGATTG

BETL1(SEQ ID NO: 7)    921 ..CTATCTA..TA.TCTATAACTAGATCTTCTGGCA...CAAATGAG.A..
BETL4(SEQ ID NO: 10)   415 ..CTGTAT...TA.TGCATGGAG.GATCG.CAGGCA..TTAATTAA.ACT
BETL2(SEQ ID NO: 8)   1447 ..ATAGATAGACA.TAGATAGATAGATGGACTGGTAGATAGATTAAGAGA
BETL3(SEQ ID NO: 9)    658 GACCGATATCGAAACTTCATCTCGAGATAT.CAAGCAATTAATGTAGGACA

BETL1(SEQ ID NO: 7)    961 ..TGTGC.....TAGAGATGGATTCGTCTTCTAT...ATAAGTACAAGTG
BETL4(SEQ ID NO: 10)   454 C.TGGAG.....TCCTTGTGACTTCCCCTTCCCT...ATAAATTCCACTA
BETL2(SEQ ID NO: 8)   1494 CATGGAGATAGATAGACACGGATAGATGTTTAGT...ATATAAAGCAG.G
BETL3(SEQ ID NO: 9)    707 CATACAA.....TAGATTTGCCTAACCATCCCCTTGTATCAGTCCATCCA

BETL1 (SEQ ID NO: 7)  1001 AG..ATCAAAGA.CGGAGATTAGAACAAACAA...ATCATATAA......
BETL4 (SEQ ID NO: 10)  495 CGT.ATGCTCGAACTGCCAATAGAACATCAAC...TTTAGATTCTTGTT.
BETL2 (SEQ ID NO: 8)  1540 CGTGCTGATATCAAACACATCAACACATTTTTGTATTAGACTATTGTAG
BETL3 (SEQ ID NO: 9)   752 TCTATAAATATATCTGCACACACCACCACAGCAGGTTGATAAAAGCAC

BETL1 (SEQ ID NO: 7)        ........................
BETL4 (SEQ ID NO: 10)       ........................
BETL2 (SEQ ID NO: 8)  1590 CTCATATCATCTGTCACCCATG
BETL3 (SEQ ID NO: 9)   802 CTCATCCC...............
```

BASAL ENDOSPERM TRANSFER CELL LAYER (BETL) SPECIFIC GENES

The application is a divisional application of application Ser. No. 09/647,376, filed on Mar. 26, 2001, now abandoned, hereby incorporated by reference and for which priority is claimed under 35 USC §120. application Ser. No. 09/647,376 is the national phase of PCT International Application No. PCT/EP99/02063, filed on Mar. 26, 1999 under 35 USC §371. The above-identified applications are hereby incorporated by reference. This application also claims priority of Application No. 9810 5628.6, filed in Europe on Mar. 27, 1998 under 35 USC §119.

The present invention-relates to nucleic acid molecules encoding basal endosperm transfer cell layer (BETL) specific proteins as well as to regulatory sequences which naturally regulate the expression of such nucleic acid molecules. The present invention also provides vectors comprising said nucleic acid molecules, wherein the nucleic acid molecules are operatively linked to regulatory elements allowing expression in prokaryotic and/or eukaryotic host cells as well as proteins encoded by said nucleic acid molecules, antibodies to said proteins and methods for their production. The present invention also relates to recombinant DNA molecules and vectors comprising said regulatory sequences as well as to host cells transformed therewith. The present invention further relates to kits and diagnostic compositions comprising the aforementioned nucleic acid molecules, proteins, antibodies, regulatory sequences, recombinant DNA molecules and vectors as well as antibodies. The present invention also relates to methods for the identification of compounds being capable of activating or inhibiting the expression of BETL specific genes. Furthermore, the present invention relates to transgenic plant cells, plant tissue and plants containing the above-described nucleic acid molecules, regulatory sequences, recombinant DNA molecules and vectors as well as to the use of the aforementioned nucleic acid molecules, regulatory sequences, recombinant DNA molecules, vectors, proteins, antibodies and/or compounds identified by the method of the invention in plant cell and tissue culture, plant breeding and/or agriculture.

There are many examples in the literature of isolated plant promoters which display tissue-specific expression when introduced into transgenic plants. In most cases these experiments have been carried out in one of a few model plant species such as *Nicotiana tabacum* or *Arabidopsis thaliana*. However, there are still relatively few examples of promoters from monocotyledonous species such as maize, which have been shown to retain their specificity when introduced back into the homologous host or into tobacco or Arabidopsis. Although there are examples of promoters which retained their endosperm-specific expression pattern when expressed as reporter constructs in transgenic tobacco, these have all conferred crown cell and not basal cell sites of expression. Thus, genes possessing basal cell-specific expression terminal hair-cell specific expression have not been described. The provision of such genes and in particular their regulatory sequences may have applications in several aspects of agriculture, in particular conferring antipathogenic/predator characteristics to transgenic plants.

Thus, the technical problem underlying the present invention was to comply with the need for genes and their regulatory sequences which are specific for a certain tissue and/or cells hitherto not available.

The solution to the technical problem is achieved by providing the embodiments characterized in the claims.

Accordingly, the invention relates to a nucleic acid molecule encoding a basal endosperm transfer cell layer (BETL) specific protein or encoding a biologically active fragment of such a protein, selected from the group consisting of:
(a) nucleic acid molecules comprising a nucleotide sequence encoding a protein comprising the amino acid sequence as given in SEQ ID NO: 2, 4 or 6;
(b) nucleic acid molecules comprising a nucleotide sequence as given in SEQ ID NO: 1, 3 or 5;
(c) nucleic acid molecules hybridizing with the complementary strand of a nucleic acid molecule as defined in (a) or (b);
(d) nucleic acid molecules, the nucleotide sequence of which is degenerate as a result of the genetic code to a nucleotide sequence of a nucleic acid molecule as defined in any one of (a) to (c); and
(e) nucleic acid molecules encoding a fragment of a protein encoded by a nucleic acid molecule of any one of (a) to (d).

The term "basal endosperm transfer cell layer (BETL) specific protein", as used herein, means that said protein or its encoding gene is to be predominantly, preferably exclusively expressed in basal region of the endosperm. This area is highly specialized to facilitate uptake of solutes during grain development. The endosperm is the main storage organ in maize seeds, nourishing the embryo while the seed develops and providing nutrients to the seedling on germination. Thus, the uptake of assimilates by the growing endosperm is a critical process in seed development. There is no symplastic connection between maternal and embryonic tissues (Thorne, 1985); instead, phloem unloading releases nutrients into an apoplastic space. Uptake of nutrients by the endosperm from this space is facilitated by the conversion of the cells at the base of the endosperm to transfer cells, which possess anatomical modifications such as the presence of extensive cell wall ingrowths to increase the membrane surface and therefore the transport capacity (Pate and Gunning, 1972). The absence of this layer is correlated with reduced rates of grain filling and eventual abortion of the seeds (Brink and Cooper, 1947; Charlton et al., 1995). Usually, said genes involved in this type of endosperm development are expressed between 8 to 20 days after pollination (DAP). Previously, a cDNA clone (BETL-1) was isolated from a cDNA bank constructed from 10 DAP maize endosperm mRNA and has been characterized in detail (Hueros et al., Plant Cell 7 (1995), 747–757). In accordance with the present invention three other cDNAs the underlying mRNA of which is specifically expressed in the basal endosperm transfer cell layer have been isolated, designated BETL-2, BETL-3 and BETL-4, respectively. Their nucleotide and amino acid sequences are depicted in SEQ ID NOS: 1, 3 and 5 and SEQ ID NOS: 2, 4 and 6, respectively, and show no obvious sequence or structural homology to the BETL-1 protein and its encoding cDNA. Taking a closer look, BETL-1 and BETL-2 protein share, however, some common features: the deduced amino acid sequences comprise small proteins with calculated MW of 7 kD. The sequences start with a hydrophobic region which is characteristic of a signal peptide and the encoded proteins are cysteine rich. The BETL-1 polypeptide contains one copy of the extensin motif, SPPPP and is found in cell wall fractions. The function of BETL-2 remains to be elucidated, however the protein has two interesting features, a potential glycosylation site and the possibility of numerous disulphide bond formations. Neither BETL-1 nor BETL-2 share obvious similarities with sequences in current databases. BETL-1 and BETL-2 have sequence homology to the defensin supergene family of antimicrobal peptides, and share weak sequence relatedness with each other. Studies which had been carried out in accordance with the present invention further revealed that BETL-2 was processed both N and C-terminally to give two products differing in size by 3 kDa.

BETL-4 is not related in sequence to the other three, but has weak sequence homology to the Bowman-Birk family of proteinase/alpha-amylase inhibitors. No enzyme inhibition role for the BETL-4 protein has yet been shown, however. Apart from the basal endosperm, there are no other sites of expression of the BETL-1 to 4 genes in maize, but similar proteins (defensins and Bowman—Birk type inhibitors) are likely to be present in other parts of the plant. Defensin have been reported from apical buds, pistils and pollen of other plant species, for example.

By "hybridizing" it is meant that such nucleic acid molecules hybridize under conventional hybridization conditions, preferably under stringent conditions such as described by, e.g., Sambrook (Molecular Cloning; A Laboratory Manual, 2nd Edition, Cold Spring Harbor Laboratory Press, Cold Spring Harbor, N.Y. (1989)).

From the above, it is evident that the nucleotide sequences depicted in SEQ ID NO: 1, 3 and 5 encode novel BETL proteins. By the provision of the nucleotide sequence as well as those encoding the amino acid sequences depicted in SEQ ID NOS: 2, 4 and 6, it is possible to isolate identical or similar nucleic acid molecules which encode BETL proteins from other species or organisms.

Thus, the present invention also relates to nucleic acid molecules hybridizing with the above-described nucleic acid molecules, and differ in one or more positions in comparison with these as long as they encode a BETL proteins. Such molecules comprise those which are fragments, analogues or derivatives of the BETL protein of the invention and differ, for example, by way of amino acid and/or nucleotide deletion(s), insertion(s), substitution(s), addition(s) and/or recombination(s) or any other modification(s) known in the art either alone or in combination from the above-described amino acid sequences or their underlying nucleotide sequence(s). Methods for introducing such modifications in the nucleic acid molecules according to the invention are well-known to the person skilled in the art. The invention also relates to nucleic acid molecules the sequence of which differs from the nucleotide sequence of any of the above-described nucleic acid molecules due to the degeneracy of the genetic code. All such fragments, analogues and derivatives of the peptide of the invention are included within the scope of the present invention, as long as the essential characteristic immunological and/or biological properties as defined above remain unaffected in kind, that is the novel nucleic acid molecules of the invention include all nucleotide sequences encoding proteins or peptides which have at least a part of the primary structural conformation for one or more epitopes capable of reacting with antibodies to BETL proteins which are encodable by a nucleic acid molecule as set forth above.

In a preferred embodiment the nucleic acid molecules according to the invention are RNA or DNA molecules, preferably cDNA, genomic DNA or synthetically synthesized DNA or RNA molecules. Preferably, the nucleic acid molecule of the invention is derived from a plant, preferably from maize. As discussed in the appended examples, the proteins encoded by the nucleic acid molecules identified according to the present invention in maize show some homology to defensin-like proteins and proteinase inhibitors. Corresponding proteins displaying similar properties should be present in other plants as well. Nucleic acid molecules of the invention can be obtained, e.g., by hybridization of the above-described nucleic acid molecules with a (sample of) nucleic acid molecule(s) of any source. Nucleic acid molecules hybridizing with the above-described nucleic acid molecules can in general be derived from any plant possessing such molecules, preferably form monocotyledonous or dicotyledonous plants, in particular from any plant of interest in agriculture, horticulture or wood culture, such as crop plants, namely those of the family Poaceae, any starch producing plants, such as potato, maniok, leguminous plants, oil producing plants, such as oilseed rape, linenseed, etc., plants using polypeptide as storage substances, such as soybean, plants using sucrose as storage substance, such as sugar beet or sugar cane, trees, ornamental plants etc. Preferably, the nucleic acid molecules according to the invention are derived from plants belonging to the family Gramineae. Nucleic acid molecules hybridizing to the above-described nucleic acid molecules can be isolated, e.g., form libraries, such as cDNA or genomic libraries by techniques well known in the art. For example, hybridizing nucleic acid molecules can be identified and isolated by using the above-described nucleic acid molecules or fragments thereof or complements thereof as probes to screen libraries by hybridizing with said molecules according to standard techniques. Possible is also the isolation of such nucleic acid molecules by applying the polymerase chain reaction (PCR) using as primers oligonucleotides derived form the above-described nucleic acid molecules.

Nucleic acid molecules which hybridize with any of the aforementioned nucleic acid molecules also include fragments, derivatives and allelic variants of the above-described nucleic acid molecules that encode a BETL protein or an immunologically or biologically active fragment thereof. Fragments are understood to be parts of nucleic acid molecules long enough to encode the described protein or a biologically or immunologically active fragment thereof as defined above.

The term "derivative" means in this context that the nucleotide sequence of these nucleic acid molecules differs from the sequences of the above-described nucleic acid molecules in one or more nucleotide positions and are highly homologous to said nucleic acid molecules. Homology is understood to refer to a sequence identity of at least 40%, particularly an identity of at least 60%, preferably more than 80% and still more preferably more than 90%. The deviations from the sequences of the nucleic acid molecules described above can, for example, be the result of nucleotide substitution(s), deletion(s), addition(s), insertion(s) and/or recombination(s); see supra.

Homology further means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other plant varieties or species, or mutations. These mutations may occur naturally or may be obtained by mutagenesis techniques. The allelic variations may be naturally occurring allelic variants as well as synthetically produced or genetically engineered variants; see supra.

The proteins encoded by the various derivatives and variants of the above-described nucleic acid molecules share specific common characteristics, such as biological activity, molecular weight, immunological reactivity, conformation, etc., as well as physical properties, such as electrophoretic mobility, chromatographic behavior, sedimentation coefficients, pH optimum, temperature optimum, stability, solubility, spectroscopic properties, etc.

Examples for the different possible applications of the nucleic acid molecules according to the invention as well as molecules derived from them will be described in detail in the following.

Hence, in a further embodiment, the invention relates to nucleic acid molecules of at least 15 nucleotides in length hybridizing specifically with a nucleic acid molecule as described above or with a complementary strand thereof. Specific hybridization occurs preferably under stringent conditions and implies no or very little cross-hybridization hybridization with nucleotide sequences encoding no or substantially different proteins. Such nucleic acid molecules may be used as probes and/or for the control of gene expression. Nucleic acid probe technology is well known to those skilled in the art who will readily appreciate that such probes may vary in length. Preferred are nucleic acid probes of 16 to 35 nucleotides in length. Of course, it may also be appropriate to use nucleic acids of up to 100 and more nucleotides in length. The nucleic acid probes of the invention are useful for various applications. On the one hand, they may be used as PCR primers for amplification of nucleic acid sequences according to the invention. Another application is the use as a hybridization probe to identify nucleic acid molecules hybridizing with a nucleic acid molecule of the invention by homology screening of genomic DNA or cDNA libraries. Nucleic acid molecules according to this preferred embodiment of the invention which are complementary to a nucleic acid molecule as described above may also be used for repression of expression of a BETL specific gene, for example due to an antisense or triple helix effect or for the construction of appropriate ribozymes (see, e.g., EP-B1 0 291 533, EP-A1 0 321 201, EP-A2 0 360 257) which specifically cleave the (pre)-mRNA of a gene comprising a nucleic acid molecule of the invention or part thereof. Selection of appropriate target sites and corresponding ribozymes can be done as described, for example, in Steinecke, Ribozymes, Methods in Cell Biology 50, Galbraith et al. eds Academic Press, Inc. (1995), 449–460. Furthermore, the person skilled in the art is well aware that it is also possible to label such a nucleic acid probe with an appropriate marker for specific applications, such as for the detection of the presence of a nucleic acid molecule of the invention in a sample derived from an organism, in particular plants.

The above described nucleic acid molecules may either be DNA or RNA or a hybrid thereof. Furthermore, said nucleic acid molecule may contain, for example, thioester bonds and/or nucleotide analogues, commonly used in oligonucleotide anti-sense approaches. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell.

Furthermore, the so-called "peptide nucleic acid" (PNA) technique can be used for the detection or inhibition of the expression of a nucleic acid molecule of the invention. For example, the binding of PNAs to complementary as well as various single stranded RNA and DNA nucleic acid molecules can be systematically investigated using thermal denaturation and BIAcore surface-interaction techniques (Jensen, Biochemistry 36 (1997), 5072–5077). Furthermore, the nucleic acid molecules described above as well as PNAs derived therefrom can be used for detecting point mutations by hybridization with nucleic acids obtained from a sample with an affinity sensor, such as BIAcore; see Gotoh, Rinsho Byori 45 (1997), 224–228. Hybridization based DNA screening on peptide nucleic acids (PNA) oligomer arrays are described in the prior art, for example in Weiler, Nucleic Acids Research 25 (1997), 2792–2799. The synthesis of PNAs can be performed according to methods known in the art, for example, as described in Koch, J. Pept. Res. 49 (1997), 80–88; Finn, Nucleic Acids Research 24 (1996), 3357–3363. Further possible applications of such PNAs, for example as restriction enzymes or as templates for the synthesis of nucleic acid oligonucleotides are known to the person skilled in the art and are, for example, described in Veselkov, Nature 379 (1996), 214 and Bohler, Nature 376 (1995), 578–581.

The present invention also relates to vectors, particularly plasmids, cosmids, viruses, bacteriophages and other vectors used conventionally in genetic engineering that contain a nucleic acid molecule according to the invention. Methods which are well known to those skilled in the art can be used to construct various plasmids and vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the nucleic acid molecules and vectors of the invention can be reconstituted into liposomes for delivery to target cells.

In a preferred embodiment the nucleic acid molecule present in the vector is linked to regulatory elements which allow the expression of the nucleic acid molecule in prokaryotic and/or eukaryotic cells. Expression comprises transcription of the nucleic acid molecule preferably into a translatable mRNA. Regulatory elements ensuring expression in prokaryotic and/or eukaryotic cells are well known to those skilled in the art. In the case of eukaryotic cells they comprise normally promoters ensuring initiation of transcription and optionally poly-A signals ensuring termination of transcription and stabilization of the transcript, for example, those of the 35S RNA from Cauliflower Mosaic Virus (CaMV). Other promoters commonly used are the Figwort Mosaic virus promoter, the polyubiquitin promoter, and the actin promoter for ubiquitous expression. The termination signals usually employed are from the Nopaline Synthase promoter or from the CAMV 35S promoter. A plant translational enhancer often used is the CAMV omega sequences, the inclusion of an intron (Intron-1 from the Shrunken gene of maize, for example) has been shown to increase expression levels by up to 100-fold. (Maiti et al., Transgenic Research 6 (1997), 143–156; Ni et al., Plant Journal 7 (1995), 661–676). Additional regulatory elements may include transcriptional as well as translational enhancers. Possible regulatory elements permitting expression in prokaryotic host cells comprise, e.g., the $P_L$, lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL). Advantageously the above-described vectors of the invention comprises a selectable and/or scorable marker. Selectable marker genes useful for the selection of transformed plant cells, callus, plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143–149); npt, which confers resistance to the aminoglycosides neomycin, kanamycin and paromycin (Herrera-Estrella, EMBO J. 2 (1983), 987–995) and hygro, which confers resistance to hygromycin (Marsh, Gene 32 (1984), 481–485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336–2338).

Useful scorable marker are also known to those skilled in the art and are commercially available. Advantageously, said marker is a gene encoding luciferase (Giacomin, Pl. Sci. 116 (1996), 59–72; Scikantha, J. Bact. 178 (1996), 121), green fluorescent protein (Gerdes, FEBS Lett. 389 (1996), 44–47) or β-glucuronidase (Jefferson, EMBO J. 6 (1987), 3901–3907). This embodiment is particularly useful for simple and rapid screening of cells, tissues and organisms containing a vector of the invention.

The present invention furthermore relates to host cells comprising a vector as described above or a nucleic acid molecule according to the invention wherein the nucleic acid molecule is foreign to the host cell.

By "foreign" it is meant that the nucleic acid molecule is either heterologous with respect to the host cell, this means derived from a cell or organism with a different genomic background, or is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell, in particular it is surrounded by different genes. In this case the nucleic acid molecule may be either under the control of its own promoter or under the control of a heterologous promoter. The vector or nucleic acid molecule according to the invention which is present in the host cell may either be integrated into the genome of the host cell or it may be maintained in some form extrachromosomally. In this respect, it is also to be understood that the nucleic acid molecule of the invention can be used to restore or create a mutant gene via homologous recombination (Paszkowski (ed.), Homologous Recombination and Gene Silencing in Plants. Kluwer Academic Publishers (1994)).

The host cell can be any prokaryotic or eukaryotic cell, such as bacterial, insect, fungal, plant or animal cells. Preferred fungal cells are, for example, those of the genus Saccharomyces, in particular those of the species *S. cerevisiae*.

Another subject of the invention is a method for the preparation of BETL proteins which comprises the cultivation of host cells according to the invention which, due to the presence of a vector or a nucleic acid molecule according to the invention, are able to express such a protein, under conditions which allow expression of the protein and recovering of the so-produced protein from the culture. Depending on the specific constructs and conditions used, the protein may be recovered from the cells, from the culture medium or from both. For the person skilled in the art it is well known that it is not only possible to express a native protein but also to express the protein as fusion polypeptides or to add signal sequences directing the protein to specific compartments of the host cell, e.g., ensuring secretion of the peptide into the culture medium, etc. Furthermore, such a protein and fragments thereof can be chemically synthesized and/or modified according to standard methods described, for example hereinbelow.

The present invention furthermore relates to proteins encoded by the nucleic acid molecules according to the invention or produced by the above-described method, and to biologically and/or immunologically active fragments of such BETL proteins. In this context, it is also understood that the proteins according to the invention may be further modified by conventional methods known in the art. By providing the proteins according to the present invention it is also possible to determine fragments which retain biological activity, namely the mature, processed form, with Cys-crossbridges formed in vivo. This allows the construction of chimeric proteins and peptides comprising an amino sequence derived from the protein of the invention, which is crucial for antipathogenic activity and other functional amino acid sequences, e.g. GUS marker gene (Jefferson, EMBO J. 6 (1987), 3901–3907). The other functional amino acid sequences may be either physically linked by, e.g., chemical means to the proteins of the invention or may be fused by recombinant DNA techniques well known in the art.

Furthermore, folding simulations and computer redesign of structural motifs of the protein of the invention can be performed using appropriate computer programs (Olszewski, Proteins 25 (1996), 286–299; Hoffman, Comput. Appl. Biosci. 11 (1995), 675–679). Computer modeling of protein folding can be used for the conformational and energetic analysis of detailed peptide and protein models (Monge, J. Mol. Biol. 247 (1995), 995–1012; Renouf, Adv. Exp. Med. Biol. 376 (1995), 37–45). In particular, the appropriate programs can be used for the identification of interactive sites of the protein and, if present, its receptor, its ligand or other interacting proteins by computer assistant searches for complementary peptide sequences (Fassina, Immunomethods 5 (1994), 114–120. Further appropriate computer systems for the design of protein and peptides are described in the prior art, for example in Berry, Biochem. Soc. Trans. 22 (1994), 1033–1036; Wodak, Ann. N.Y. Acad. Sci. 501 (1987), 1–13; Pabo, Biochemistry 25 (1986), 5987–5991. The results obtained from the above-described computer analysis can be used for, e.g., the preparation of peptidomimetics of the protein of the invention or fragments thereof. Such pseudopeptide analogues of the natural amino acid sequence of the protein may very efficiently mimic the parent protein (Benkirane, J. Biol. Chem. 271 (1996), 33218–33224). For example, incorporation of easily available achiral Ω-amino acid residues into a protein of the invention or a fragment thereof results in the substitution of amide bonds by polymethylene units of an aliphatic chain, thereby providing a convenient strategy for constructing a peptidomimetic (Banerjee, Biopolymers 39 (1996), 769–777). Superactive peptidomimetic analogues of small peptide hormones in other systems are described in the prior art (Zhang, Biochem. Biophys. Res. Commun. 224 (1996), 327–331). Appropriate peptidomimetics of the protein of the present invention can also be identified by the synthesis of peptidomimetic combinatorial libraries through successive amide alkylation and testing the resulting compounds, e.g., for their immunological properties. Methods for the generation and use of peptidomimetic combinatorial libraries are described in the prior art, for example in Ostresh, Methods in Enzymology 267 (1996), 220–234 and Dorner, Bioorg. Med. Chem. 4 (1996), 709–715.

Furthermore, a three-dimensional and/or crystallographic structure of the protein of the invention can be used for the design of peptidomimetic inhibitors of the biological activity of the protein of the invention (Rose, Biochemistry 35 (1996), 12933–12944; Rutenber, Bioorg. Med. Chem. 4 (1996), 1545–1558).

Furthermore, the present invention relates to antibodies specifically recognizing a BETL protein according to the invention or parts, i.e. specific fragments or epitopes, of such a protein. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of proteins according to the invention as well as for the monitoring of the synthesis of such proteins, for example, in recombinant organisms, and for the identification of compounds interacting with the protein according to the invention. For example, surface plasmon resonance as employed in the BIAcore system can be used to increase the efficiency of phage antibodies selections, yielding a high increment of affinity from a single library of phage antibodies which bind to an epitope of the protein of the invention (Schier, Human Antibodies Hybridomas 7 (1996), 97–105; Malmborg, J. Immunol. Methods 183 (1995), 7–13).

The nucleic acid molecules according to the invention are in particular useful for the genetic manipulation of plant cells in order to modify the basal endosperm transfer cell layer and to obtain plants with modified, preferably with improved or useful phenotypes. Thus, the present invention provides for a method for the production of transgenic plants, plant cells or plant tissue comprising the introduction of a nucleic acid molecule or vector of the invention into the genome of said plant, plant cell or plant tissue.

For the expression of the nucleic acid molecules according to the invention in sense or antisense orientation in plant cells, the molecules are placed under the control of regulatory elements which ensure the expression in plant cells. These regulatory elements may be heterologous or homologous with respect to the nucleic acid molecule to be expressed as well with respect to the plant species to be transformed. In general, such regulatory elements comprise a promoter active in plant cells. To obtain expression in all tissues of a transgenic plant, preferably constitutive promoters are used, such as the 35 S promoter of CaMV (Odell, Nature 313 (1985), 810–812) or promoters of the polyubiquitin genes of maize (Christensen, Plant Mol. Biol. 18 (1982), 675–689). In order to achieve expression in specific tissues of a transgenic plant it is possible to use tissue specific promoters (see, e.g., Stockhaus, EMBO J. 8 (1989), 2245–2251). Known are also promoters which are specifically active in tubers of potatoes or in seeds of different plants species, such as maize, Vicia, wheat, barley etc. Inducible promoters may be used in order to be able to exactly control expression. An example for inducible promoters are the promoters of genes encoding heat shock proteins. Also microspore-specific regulatory elements and their uses have been described (WO96/16182). Furthermore, the chemically inducible Test-system may be employed (Gatz, Mol. Gen. Genet. 227 (1991); 229–237). Further suitable promoters are known to the person skilled in the art and are described, e.g., in Ward (Plant Mol. Biol. 22 (1993), 361–366). The regulatory elements may further comprise transcriptional and/or translational enhancers functional in plants cells. Furthermore, the regulatory elements may include transcription termination signals, such as a poly-A signal, which lead to the addition of a poly A tail to the transcript which may improve its stability. In the case that a nucleic acid molecule according to the invention is expressed in sense orientation it is in principle possible to modify the coding sequence in such a way that the protein is located in any desired compartment of the plant cell. These include the endoplasmatic reticulum, the vacuole, the mitochondria, the plastids, the apoplast, the cytoplasm etc. Methods how to carry out this modifications and signal sequences ensuring localization in a desired compartment are well known to the person skilled in the art. An example is the localization in oil bodies by specific targeting (Abell, Plant Cell 9 (1997), 1481–1499) or deposition in the extracellular matrix (Herbers, Molecular Breeding 2 (1996), 81–87).

Methods for the introduction of foreign DNA into plants are also well known in the art. These include, for example, the transformation of plant cells or tissues with T-DNA using *Agrobacterium tumefaciens* or *Agrobacterium rhizogenes*, the fusion of protoplasts, direct gene transfer (see, e.g., EP-A 164 575), injection, electroporation, biolistic methods like particle bombardment and other methods known in the art. The vectors used in the method of the invention may contain further functional elements, for example "left border"- and "right border"-sequences of the T-DNA of *Agrobacterium* which allow for stably integration into the plant genome. Furthermore, methods and vectors are known to the person skilled in the art which permit the generation of marker free transgenic plants, i.e. the selectable or scorable marker gene is lost at a certain stage of plant development or plant breeding. This can be achieved by, for example cotransformation (Lyznik, Plant Mol. Biol. 13 (1989), 151–161; Peng, Plant Mol. Biol. 27 (1995), 91–104) and/or by using systems which utilize enzymes capable of promoting homologous recombination in plants (see, e.g., WO97/08331; Bayley, Plant Mol. Biol. 18 (1992), 353–361); Lloyd, Mol. Gen. Genet. 242 (1994), 653–657; Maeser, Mol. Gen. Genet. 230 (1991), 170–176; Onouchi, Nucl. Acids Res. 19 (1991), 6373–6378). Methods for the preparation of appropriate vectors are described by, e.g., Sambrook (Molecular Cloning; A Laboratory Manual, 2nd Edition (1989), Cold Spring Harbor Laboratory Press, Cold Spring Harbor, N.Y.). Suitable strains of *Agrobacterium tumefaciens* and vectors as well as transformation of *Agrobacteria* and appropriate growth and selection media are well known to those skilled in the art and are described in the prior art (GV3101 (pMK90RK), Koncz, Mol. Gen. Genet. 204 (1986), 383–396; C58C1 (pGV 3850kan), Deblaere, Nucl. Acid Res. 13 (1985), 4777; Bevan, Nucleic. Acid Res. 12(1984), 8711;

Koncz, Proc. Natl. Acad. Sci. USA 86 (1989), 8467–8471; Koncz, Plant Mol. Biol. 20 (1992), 963–976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1–22; EP-A-120 516; Hoekema: The Binary Plant Vector System, Offsetdrukkerij Kanters B. V., Alblasserdam (1985), Chapter V, Fraley, Crit. Rev. Plant. Sci., 4, 1–46; An, EMBO J. 4 (1985), 277–287). Although the use of *Agrobacterium tumefaciens* is preferred in the method of the invention, other *Agrobacterium* strains, such as *Agrobacterium rhizogenes*, may be used, for example if a phenotype conferred by said strain is desired.

Methods for the transformation using biolistic methods are well known to the person skilled in the art; see, e.g., Wan, Plant Physiol. 104 (1994), 37–48; Vasil, Bio/Technology 11 (1993), 1553–1558 and Christou (1996) Trends in Plant Science 1, 423–431. Microinjection can be performed as described in Potrykus and Spangenberg (eds.), Gene Transfer To Plants. Springer Verlag, Berlin, N.Y. (1995).

The transformation of most dicotyledonous plants is possible with the methods described above. But also for the transformation of monocotyledonous plants several successful transformation techniques have been developed. These include the transformation using biolistic methods as, e.g., described above as well as protoplast transformation, electroporation of partially permeabilized cells, introduction of DNA using glass fibers, etc.

In general, the plants which can be modified according to the invention and which either show overexpression of a protein according to the invention or a reduction of the synthesis of such a protein can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc.

Thus, the present invention relates also to transgenic plant cells which contain stably integrated into the genome a nucleic acid molecule according to the invention linked to regulatory elements which allow for expression of the nucleic acid molecule in plant cells and wherein the nucleic acid molecule is foreign to the transgenic plant cell. For the meaning of foreign; see supra.

The presence and expression of the nucleic acid molecule in the transgenic plant cells leads to the synthesis of a BETL protein which has an influence on pathogen resistance of the plant cells and leads to physiological and phenotypic changes in plants containing such cells.

Thus, the present invention also relates to transgenic plants and plant tissue comprising transgenic plant cells according to the invention. Due to the (over)expression of a BETL protein of the invention, e.g., in cellular compartments and/or plant tissue in which they do not naturally occur these transgenic plants may show various physiological, developmental and/or morphological modifications in comparison to wild-type plants. For example, these transgenic plants may display a hypersensitive response and/or altered expression of pathogenesis related genes.

Furthermore, the invention relates to a transgenic plant cell which contains stably integrated into the genome a nucleic acid molecule according to the invention or part thereof, wherein the transcription and/or expression of the nucleic acid molecule or part thereof leads to reduction of the synthesis of a BETL protein.

In a preferred embodiment, the reduction is achieved by an anti-sense, sense, ribozyme, co-suppression and/or dominant mutant effect. The provision of the nucleic acid molecules according to the invention opens up the possibility to produce transgenic plant cells with- a reduced level of the protein as described above and, thus, with a defect in the accumulation of a BETL protein. Techniques how to achieve this are well known to the person skilled in the art. These include, for example, the expression of antisense-RNA, ribozymes, of molecules which combine antisense and ribozyme functions and/or of molecules which provide for a co-suppression effect; see also supra. When using the antisense approach for reduction of the amount of BETL proteins in plant cells, the nucleic acid molecule encoding the antisense-RNA is preferably of homologous origin with respect to the plant species used for transformation. However, it is also possible to use nucleic acid molecules which display a high degree of homology to endogenously occurring nucleic acid molecules encoding a BETL protein. In this case the homology is preferably higher than 80%, particularly higher than 90% and still more preferably higher than 95%. The reduction of the synthesis of a protein according to the invention in the transgenic plant cells can result in an alteration in pathogen resistance or efficiency of solute transfer. In transgenic plants comprising such cells this can lead to various physiological, developmental and/or morphological changes.

Thus, the present invention also relates to transgenic plants comprising the above-described transgenic plant cells. These may show, for example, a reduction in pathogen resistance or a reduced efficiency of solute transfer.

The present invention also relates to cultured plant tissues comprising transgenic plant cells as described above which either show overexpression of a protein according to the invention or a reduction in synthesis of such a protein.

In yet another aspect, the invention also relates to harvestable parts and to propagation material of the transgenic plants according to the invention which either contain transgenic plant cells expressing a nucleic acid molecule according to the invention or which contain cells which show a reduced level of the described protein. Harvestable parts can be in principle any useful parts of a plant, for example, leaves, stems, fruit, seeds, roots etc. Propagation material includes, for example, seeds, fruits, cuttings, seedlings, tubers, rootstocks etc.

As described herein above the nucleic acid molecule and vectors of the invention are particularly useful for the production of plants which display an altered level of BETL protein(s) and, for example, improved disease resistance to ear pathogens such as certain Fusarium species.

As mentioned above, a further object of the present invention is the provision of means and methods for specifically expressing heterologous proteins and modulating gene expression in certain cells and tissues, in particular in specific cells of the endosperm.

Accordingly, the invention also relates to a regulatory sequence of a promoter naturally regulating the expression of a nucleic acid molecule of the invention described above or of a nucleic acid molecule homologous to a nucleic acid molecule of the invention, said regulatory sequence being capable of conferring expression in basal endosperm transfer layer cells.

In context with the present invention, the term "regulatory sequence" refers to sequences which influence the specificity and/or level of expression, for example in the sense that they confer cell and/or tissue specificity. Such regions can be located upstream of the transcription initiation site, but can also be located downstream of it, e.g., in transcribed but not translated leader sequences.

The term "promoter", within the meaning of the present invention refers to nucleotide sequences necessary for transcription initiation, i.e. RNA polymerase binding, and may also include, for example, the TATA box.

The term "nucleic acid molecule homologous to a nucleic acid molecule of the invention", as used herein includes promoter regions and regulatory sequences of other BETL genes, such as the gene encoding the BETL-1 protein as well as genes from other species, for example, sorghum, millet, coix, barley, wheat and rice which are homologous to the maize BETL genes and which display substantially the same expression pattern. Such promoters are characterized by their capability of conferring expression of a heterologous DNA sequence in substantially all basal endosperm transfer layer cells.

Thus, according to the present invention, regulatory sequences from other species can be used that are functionally homologous to the regulatory sequences of the promoter of the above defined BETL specific nucleic acid molecules, or promoters of genes that display an identical or similar pattern of expression, in the sense of being expressed in basal endosperm transfer layer cells. However, the expression conferred by the regulatory sequences of the invention may not be limited to basal endosperm transfer cells but can include or be restricted to, for example, aerial hair cells, terminal (gland) cell, testa/pericarp of the developing seed, hyathodes on true leaves, stigmatic papillar cells and seed. The particular expression pattern may also depend on the plant/vector system employed. However, expression of heterologous DNA sequences driven by the regulatory sequences of the invention predominantly occurs in the basal endosperm transfer layer cells unless certain elements of the regulatory sequences of the invention, such as described below were taken and designed by the person skilled in the art to control the expression of a heterologous DNA sequence in one of the above described cell types. The endosperm is a triploid tissue composed mainly of two types of cells, the central endosperm cells which accumulate starch and proteins, and outer aleurone cells. Aleurone cell differentiation takes place between 6 and 10 days after pollination, producing a single cell layer of small round cells that accumulate spherosomes and protein bodies. Endosperm transfer cells develop by modification of the outer cell layers adjacent to the pedicel. The most basal layer consists of a sheet of elongated cells densely covered by cell wall ingrowths, and two or three adjacent endosperm cell layers also possess cell wall ingrowths, successively decreasing in extent towards the center of the kernel (Schell et al., 1984; Shannon et al., 1986; Davis et al., 1990). To date, physiological and cytological studies have been reported for basal cells, but little is known about the regulation of development of the transfer cell phenotype. A possible effect of genomic imprinting on transfer layer development has been reported (Charlton et al., 1995) A number of genes specifically expressed in different seed tissues have been isolated, their corresponding promoter sequences have been functionally analyzed and, in some cases, sequences conferring tissue specificity have been identified for both, endosperm (Giovonazzo et al., 1992; Quayle and Feix, 1992; Thompson et al, 1990, Muller and Knudsen, 1993) and aleurone (Kalla et al, 1994; Leah et al., 1994). In contrast, only two transfer cell specific cDNAs have been isolated, BETL-1 in maize (synonymous BET-1, Hueros et al., 1995) and END-1 in barley (Doan et al., 1996), and the basis for transfer cell-specific expression was unknown.

In accordance with the present invention, novel regulatory sequences of BETL genes, designated BETL-1, BETL-2, BETL-3 and BETL-4, respectively, (see supra) have been isolated and it has been surprisingly found that these regulatory sequences comprising the nucleotide sequences depicted in SEQ ID NOS: 7 to 10, respectively, contain element(s) that alone is/are sufficient and necessary for conferring expression in basal endosperm transfer layer cells and related cells. In order to identify the regulatory sequences and specific elements of the BETL genes, 5'-upstream genomic fragments were cloned in front of the GUS coding region and the resulting chimeric genes were introduced by means of Agrobacterium tumefaciens mediated gene transfer into tobacco plants. The expression pattern observed in the transgenic plants containing the GUS marker gene under the control of the regulatory sequences of the invention revealed expression in aerial hair cells and the terminal (gland) cell; see FIGS. 6 and 7. Expression was also observed in fused testa/pericarp of the developing seed from 1–2 days after pollination, peaking at ca. 10 DAP and declining to zero by ca. 18 DAP, thus resembling the expression pattern of the native BETL genes; see FIG. 5.

Full-length promoter/GUS constructs were also introduced into Arabidopsis. The pattern of expression in these transgenic plants was hyathodes on true leaves, stigmatic papillar cells, seed coat and weaker expression in developing embryo. The experiments performed in accordance with the present invention revealed that seed and leaf hair-specific expression can be conferred by a promoter fragment of 250 bp and that the leaf hair activity is retained in an 86 bp promoter fragment; see FIG. 12. In Arabidopsis, seedcoat expression was observed with the full length promoter and a fragment of 800 bp, but not with the 250 bp deletion; see also FIG. 12. Moreover, it could be shown that the expression of the chimeric gene containing said regulatory sequences correspond to the endogenous BETL expression in the endosperm. Thus, the regulatory sequences of the invention can be used to drive the expression of heterologous DNA sequences specifically in endosperm basal transfer layer cells, terminal hair cells and testa. In fact, the regulatory sequences of the invention appear to be capable of conferring expression with higher specificity for certain cells than it is observed for the natural BETL genes.

It is now possible for the person skilled in the art to isolate with the help of the regulatory sequences of the invention corresponding genes from other species, for example, barley. This can be done by conventional techniques known in the art, for example, by using the regulatory sequences depicted in any one of SEQ ID NOS 7 to 10 as a hybridization probe or by designing appropriate PCR primers. It is then possible to isolate the corresponding promoter region by conventional techniques and test it for its expression pattern. For this purpose, it is, for instance, possible to fuse the promoter to a reporter gene, such as GUS, luciferase or green fluorescent protein (GFP) and assess the expression of the reporter gene in transgenic plants. The present invention also relates to regulatory sequences which are substantially identical to those of any one of SEQ ID NOS 7 to 10 or which are homologous thereto by way of their structure or to parts thereof and which are able to confer specific expression in basal endosperm transfer cells.

Such regulatory sequences differ at one or more positions from the above-mentioned regulatory sequences but still have the same specificity, namely they comprise the same or similar sequence motifs, preferably 6 to 10 nucleotides in length, responsible for the above described expression pattern to which the one(s) printed in bold in FIG. 13 are expected to belong. Preferably such regulatory sequences hybridize to one of the above-mentioned regulatory sequences, most preferably under stringent conditions. Particularly preferred are regulatory sequences which share at least 85%, more preferably 90–95%, and most preferably 96–99% sequence identity with one of the above-mentioned regulatory sequences and have the same or substantially the same specificity. Such regulatory sequences also comprise those which are altered, for example by nucleotide deletion(s), insertion(s), substitution(s), addition(s), and/or recombination(s) and/or any other modification(s) known in the art either alone or in combination in comparison to the above-described nucleotide sequence. Methods for introducing such modifications in the nucleotide sequence of the regulatory sequences of the invention are well known to the person skilled in the art. It is also immediately evident to the person skilled in the art that further regulatory elements may be added to the regulatory sequences of the invention. For example, transcriptional enhancers and/or sequences which allow for induced expression of the regulatory sequences of the invention may be employed. A suitable inducible system is for example tetracycline-regulated gene expression as described, e.g., by Gatz, supra.

In one embodiment the regulatory sequence of the invention comprises a a DNA sequence selected from the group consisting of
(a) DNA sequences comprising a nucleotide sequence as depicted in any one of SEQ ID NOS 7 to 10 or (a) part(s) thereof;
(b) DNA sequences comprising nucleotides 1 to 1615 or 1350 to 1615 of the nucleotide sequence as depicted in SEQ ID NO: 8;
(c) DNA sequences comprising at least one nucleotide sequence printed in bold and of 6 to 10 nucleotides in length of a nucleotide sequence shown in FIG. 13;
(d) DNA sequences hybridizing with a nucleotide sequence as defined in (a), (b) or (c) under stringent conditions; and
(e) DNA sequences comprising nucleotide sequences which are conserved in (a), (b), (c) and (d).

DNA sequences comprising nucleotides 1 to 1615 of SEQ ID No. 8 confer BETL-specific expression in transgenic maize. DNA sequences comprising as little as 1350 to 1615 of minimal BETL-2 promoter fragment (1350–1615 of SEQ ID No. 8) cloned by PCR using Nco1 and Kpn1 primers into pRT 103 vector to produce a translational fusion and subsequently into pBin19 HinD111—SSt1 for plant transformation was sufficient to confer seed coat and leaf hair specific expression in transgenic tobacco. Therefore, minimum regulatory sequences necessary are located in the last 365 bp of SEQ ID No.8.

The potential exists to modify the regulatory sequences as depicted in SEQ ID NOS. 7 to 10 or sequence motifs thereof by, e.g., nucleotide replacements which do not affect the overall structure or binding motif of the regulatory sequence so that it remains capable of conferring BETL specific gene expression as defined above.

The regulatory sequence of the invention may be derived from the BETL genes of maize (see Examples) although other plants may be suitable sources for such regulatory sequences as well.

Usually, said regulatory sequence is part of a recombinant DNA molecule. In a preferred embodiment of the present invention, the regulatory sequence in the recombinant DNA molecule is operatively linked to a heterologous DNA sequence. The term heterologous with respect to the DNA sequence being operatively linked to the regulatory sequence of the invention means that said DNA sequence is not naturally linked to the regulatory sequence of the invention. Expression of said heterologous DNA sequence comprises transcription of the DNA sequence, preferably into a translatable mRNA. Regulatory elements ensuring expression in eukaryotic cells, preferably plant cells, are well known to those skilled in the art. They usually comprise poly-A signals ensuring termination of transcription and stabilization of the transcript, see also supra. Additional regulatory elements may include transcriptional as well as translational enhancers; see supra.

In a preferred embodiment, the heterologous DNA sequence of the above-described recombinant DNA molecules encodes a peptide, protein, antisense RNA, sense RNA and/or ribozyme. The recombinant DNA molecule of the invention can be used alone or as part of a vector to express heterologous DNA sequences, which, e.g., encode proteins for, e.g., the control of disease resistance, modulation of nutrition value or diagnostics of BETL related gene expression. The recombinant DNA molecule or vector containing the DNA sequence encoding a protein of interest is introduced into the cells which in turn produce the protein of interest. For example, the regulatory sequences of the invention can be operatively linked to sequences encoding Barstar and Barnase, respectively, for use in the production of male and female sterility in plants.

On the other hand, said protein can be a scorable marker, e.g., luciferase, green fluorescent protein or β-galactosidase. This embodiment is particularly useful for simple and rapid screening methods for compounds and substances described herein below capable of modulating BETL specific gene expression. For example, developing seeds can be cultured in the presence and absence of a candidate compound in order to determine whether the compound affects the expression of genes which are under the control of regulatory sequences of the invention, which can be measured, e.g., by monitoring the expression of the above-mentioned marker. It is also immediately evident to those skilled in the art that other marker genes may be employed as well, encoding, for example, a selectable marker which provides for the direct selection of compounds which induce or inhibit the expression of said marker.

The regulatory sequences of the invention may also be used in methods of antisense approaches. The antisense RNA may be a short (generally at least 10, preferably at least 14 nucleotides, and optionally up to 100 or more nucleotides) nucleotide sequence formulated to be complementary to a portion of a specific mRNA sequence and/or DNA sequence of the gene of interest. Standard methods relating to antisense technology have been described; see, e.g., Klann, Plant Physiol. 112 (1996), 1321–1330. Following transcription of the DNA sequence into antisense RNA, the antisense RNA binds to its target sequence within a cell, thereby inhibiting translation of the mRNA and downregulating expression of the protein encoded by the mRNA.

In a further embodiment, the invention relates to nucleic acid molecules of at least 15 nucleotides in length hybridizing specifically with a regulatory sequence as described above or with a complementary strand thereof. Specific hybridization occurs preferably under stringent conditions and implies no or very little cross-hybridization with nucleotide sequences having no or substantially different regulatory properties. Such nucleic acid molecules may be used as probes and/or for the control of gene expression. Nucleic acid probe technology is well known to those skilled in the art who will readily appreciate that such probes may vary in length. Preferred are nucleic acid probes of 17 to 35 nucleotides in length. Of course, it may also be appropriate to use nucleic acids of up to 100 and more nucleotides in length. The nucleic acid probes of the invention are useful for various applications. On the one hand, they may be used as PCR primers for amplification of regulatory sequences according to the invention. Another application is the use as a hybridization probe to identify regulatory sequences hybridizing to the regulatory sequences of the invention by homology screening of genomic DNA libraries. Nucleic acid molecules according to this preferred embodiment of the invention which are complementary to a regulatory sequence as described above may also be used for repression of expression of a gene comprising such regulatory sequences, for example due to an antisense or triple helix effect or for the construction of appropriate ribozymes (see, e.g., EP-B1 0 291 533, EP-A1 0 321 201, EP-A2 0 360 257) which specifically cleave the (pre)-mRNA of a gene comprising a regulatory sequence of the invention. Selection of appropriate target sites and corresponding ribozymes can be done as described for example in Steinecke, Ribozymes, Methods in Cell Biology 50, Galbraith et al. eds Academic Press, Inc. (1995), 449–460. Furthermore, the person skilled in the art is well aware that it is also possible to label such a nucleic acid probe with an appropriate marker for specific applications, such as for the detection of the presence of a nucleic acid molecule of the invention in a sample derived from an organism. The above described nucleic acid molecules may either be DNA or RNA or a hybrid thereof. Furthermore, said nucleic acid molecule may contain, for example, thioester bonds and/or nucleotide analogues, commonly used in oligonucleotide anti-sense approaches. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. Such nucleic acid molecules may further contain ribozyme sequences which specifically cleave the (pre)-mRNA comprising the regulatory sequence of the invention.

The present invention also relates to vectors, particularly plasmids, cosmids, viruses and bacteriophages used conventionally in genetic engineering that comprise a recombinant DNA molecule of the invention. Preferably, said vector is an expression vector and/or a vector further comprising a selection marker for plants. For example of suitable selector markers, see supra. Methods which are well known to those skilled in the art can be used to construct recombinant vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the recombinant DNA molecules and vectors of the invention can be reconstituted into liposomes for delivery to target cells.

The present invention furthermore relates to host cells transformed with a regulatory sequence, a DNA molecule or vector of the invention. Said host cell may be a prokaryotic or eukaryotic cell. The regulatory sequence, vector or recombinant DNA molecule of the invention which is present in the host cell may either be integrated into the genome of the host cell or it may be maintained extrachromosomally. The host cell can be any prokaryotic or eukaryotic cell, such as a bacterial, insect, fungal, plant, animal or human cell. Preferred cells are plant cells.

In a further preferred embodiment, the present invention provides for a method for the production of transgenic plants, plant cells or plant tissue comprising the introduction of a nucleic acid molecule, recombinant DNA molecule or vector of the invention into the genome of said plant, plant cell or plant tissue. For the expression of the heterologous DNA sequence under the control of the regulatory sequence according to the invention in plant cells, further regulatory sequences such as poly A tail may be fused, preferably 3' to the heterologous DNA sequence, see also supra. Further possibilities might be to add Matrix Attachment Sites at the borders of the transgene to act as "delimiters" and insulate against methylation spread from nearby heterochromatic sequences. Methods for the introduction of foreign DNA into plants, plant cells and plant tissue are described above.

Thus, the present invention relates also to transgenic plant cells which contain stably integrated into the genome a recombinant DNA molecule or vector according to the invention.

Furthermore, the present invention also relates to transgenic plants and plant tissue comprising the above-described transgenic plant cells. These plants may show, for example, increased rate of solute transfer.

In yet another aspect the invention also relates to harvestable parts and to propagation material of the transgenic plants according to the invention which contain transgenic plant cells described above. Harvestable parts can be in principle any useful part of a plant, for example, leaves, stems, fruit, seeds, roots etc. Propagation material includes, for example, seeds, fruits, cuttings, seedlings, tubers, rootstocks etc.

With the regulatory sequences of the invention, it is now possible to study in vivo BETL specific gene expression. Furthermore, since BETL specific gene expression has different patterns in different stages of physiological and pathological conditions, it is now possible to determine further regulatory sequences which may be important for the up- or down-regulation of BETL gene expression, for example in response to sugars or elicitors. In addition, it is now possible to in vivo study mutations which affect different functional or regulatory aspects of specific gene expression in endosperm development.

The in vivo studies referred to above will be suitable to further broaden the knowledge on the mechanisms involved in grain filling, and the mode(s) of action of BETL proteins. To date nothing is known about the activity, nature or mode of act ion of antipathogenic proteins in the transfer layer or about the role played by the transfer cell-specific proteins in cell wall and plamalemma modifications. Expression of heterologous genes or antisense RNA under the control of the regulatory sequence of the present invention in developing seed may allow the understanding of the function of each of these proteins in the plant.

The present invention further relates to a method for the identification of an activator or inhibitor of genes specifically expressed in basal endosperm transfer layer cells comprising the steps of:

(a) providing a plant, plant cell, or plant tissue comprising a recombinant DNA molecule comprising a readout system operatively linked to a regulatory sequence of the invention;

(b) culturing said plant cell or tissue or maintaining said plant in the presence of a compound or a sample comprising a plurality of compounds under conditions which permit expression of said readout system;

(c) identifying or verifying a sample and compound, respectively, which leads to suppression or activation and/or enhancement of expression of said readout system in said plant, plant cell, or plant tissue.

The term "read out system" in context with the present invention means a DNA sequence which upon transcription and/or expression in a cell, tissue or organism provides for a scorable and/or selectable phenotype. Such read out systems are well known to those skilled in the art and comprise, for example, recombinant DNA molecules and marker genes as described above.

The term "plurality of compounds" in a method of the invention is to be understood as a plurality of substances which may or may not be identical. Said compound or plurality of compounds may be comprised in, for example, samples, e.g., cell extracts from, e.g., plants, animals or microorganisms. Furthermore, said compound(s) may be known in the art but hitherto not known to be capable of suppressing or activating and/or enhancing the transcription of a BETL specifically expressed gene. The plurality of compounds may be, e.g., added to the culture medium or injected into the plant, plant cells or tissue. If a sample containing a compound or a plurality of compounds is identified in the method of the invention, then it is either possible to isolate the compound from the original sample identified as containing the compound capable of suppressing or activating and/or enhancing the transcription of a BETL specific expressed gene, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. Preferably, the compound identified according to the above described method is further formulated in a form suitable for the application in plant breeding or plant cell and tissue culture.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879–880; Hupp, Cell 83 (1995), 237–245; Gibbs, Cell 79 (1994), 193–198 and references cited supra). Furthermore, genes encoding a putative regulator of BETL gene and/or which are located up- or downstream the endosperm developmental pathway may be identified using, for example, insertion mutagenesis using, for example, gene targeting vectors known in the art (see, e.g., Hayashi, Science 258 (1992), 1350–1353; Fritze and Walden, Gene activation by T-DNA tagging. In *Methods in Molecular biology* 44 (Gartland, K. M. A. and Davey, M. R., eds). Totowa: Human Press (1995), 281–294) or transposon tagging (Chandlee, Physiologia Plantarum 78 (1990), 105–115). Said compounds can also be functional derivatives or analogues of known inhibitors or activators. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, N.Y., USA. Furthermore, said derivatives and analogues can be tested for their effects according to methods known in the art. Furthermore, peptidomimetics and/or computer aided design of appropriate derivatives and analogues can be used, for example, according to the methods described above.

In a preferred embodiment of the method of the invention said recombinant DNA molecule comprising said read out system is a recombinant DNA molecule of the invention as described in the embodiments hereinbefore.

In a further preferred embodiment of the method of the invention said plant or plant cell or tissue is a plant, plant cell or tissue of the invention described in the embodiments hereinbefore.

Determining whether a compound is capable of suppressing or activating and/or enhancing the transcription of a BETL specific gene can be done, for example, in plants or seeds by monitoring the reporter gene. It can further be done by monitoring the phenotypic characteristics of the transgenic plant of the invention contacted with the compounds and compare it to that of wild-type plants. In an additional embodiment, said characteristics may be compared to that of a transgenic plant contacted with a compound which is either known to be capable or incapable of suppressing or activating and/or enhancing BETL specific gene expression. The compounds identified according to the method of the invention are expected to be very beneficial since promoters that have been used so far are only of limited use due to the non or not tightly regulated tissue specificity of their regulatory sequences.

The inhibitor or activator identified by the above-described method may prove useful as a herbicide, pesticide and/or as a plant growth regulator. Thus, in a further embodiment the invention relates to a compound obtained or identified according to the method of the invention said compound being an activator of BETL specific gene expression and/or function or an inhibitor of BETL specific gene expression and/or function.

Such useful compounds can be for example transacting factors which bind to the regulatory sequence of the invention. Identification of transacting factors can be carried out using standard methods in the art (see, e.g., Sambrook, supra, and Ausubel, supra). To determine whether a protein binds to the regulatory sequences of the invention, standard DNA footprinting and/or native gel-shift analyses can be carried out. In order to identify a transacting factor which binds to the regulatory sequence of the invention, the regulatory sequence can be used as an affinity reagent in standard protein purification methods, or as a probe for screening an expression library. Once the transacting factor is identified, modulation of its binding to the regulatory sequences of the invention can be pursued, beginning with, for example, screening for inhibitors against the binding of the transacting factor to the regulatory sequences of the present invention. Activation or repression of BETL specific genes could then be achieved in plants by applying of the transacting factor (or its inhibitor) or the gene encoding it, e.g. in a vector for transgenic plants. In addition, if the active form of the transacting factor is a dimer, dominant-negative mutants of the transacting factor could be made in order to inhibit its activity. Furthermore, upon identification of the transacting factor, further components in the pathway leading to activation (e.g. signal transduction) or repression of a gene under the control of the regulatory sequences of the present invention can then be identified. Modulation of the activities of these components can then be pursued, in order to develop additional drugs and methods for modulating the expression of a gene under the control of the regulatory sequences of the present invention.

Besides the identification of transacting factors it is also immediately evident to the person skilled in the art that antibodies can be raised against the regulatory sequences of the invention or against the compounds identified according to the method of the present invention. Thus, the present invention also relates to an antibody specifically recognizing a regulatory sequence of the invention or the compound identified according to the method of the present invention. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. Furthermore, antibodies or fragments thereof to the aforementioned BETL specific expressed gene products can be obtained by using methods which are described, e.g., in Harlow and Lane "Antibodies, A Laboratory Manual", CSH Press, Cold Spring Harbour, 1988. These antibodies may be monoclonal antibodies, polyclonal antibodies or synthetic antibodies as well as fragments of antibodies, such as Fab, Fv, or scFv fragments etc.

The invention also relates to a diagnostic composition comprising at least one of the aforementioned nucleic acid molecules and/or comprising a nucleic acid molecule which is complementary for such a nucleic acid molecule, a vector of the invention, a BETL protein of the invention or an immunologically or biologically active fragment thereof or an antibody specifically recognizing such a protein or fragment; a regulatory sequence or recombinant DNA, or a corresponding vector of the invention, a compound designed orientated according to the protein of the invention and/or identified according to the method described above and/or an antibody specifically recognizing such a compound or a regulatory sequence of the invention, and optionally suitable means for detection.

Said diagnostic compositions may be used for methods for detecting expression of a BETL specific protein by detecting the presence of mRNA encoding a protein expressed in basal endosperm transfer layer cells which comprises isolation of mRNA from a cell and contacting the mRNA so obtained with a probe comprising a nucleic acid probe as described above under hybridizing conditions, detecting the presence of mRNA hybridized to the probe, and thereby detecting the expression of the protein by the cell.

Further methods of detecting the presence of a protein according to the present invention comprises immunotechniques well known in the art, for example enzyme linked immunosorbent assay.

Moreover, the present invention relates to a kit comprising at least one of the aforementioned nucleic acid molecules, vectors, proteins, compounds or antibodies of the invention. The kit or its ingredients according to the invention can be used in plant cell and plant tissue cultures, for example to detect expression levels of the transgene. The kit and its application is particularly useful to screen for antipathogenic effects in fungal cultures. The kit of the invention and its ingredients are expected to be very useful in breeding new varieties of, for example, plants which display improved properties such as nutritial value or disease resistance.

It is also immediately evident to the person skilled in the art that the regulatory sequences, recombinant DNA molecules, vectors and compounds of the present invention can be employed to produce transgenic plants with a desired trait (see for review TIPTEC Plant Product & Crop Biotechnology 13 (1995), 312–397) comprising (i) herbicide tolerance (DE-A-3701623; Stalker, Science 242 (1988), 419), (ii) insect resistance (Vaek, Plant Cell 5 (1987), 159–169), (iii) virus resistance (Powell, Science 232 (1986), 738–743; Pappu, World Journal of Microbiology & Biotechnology 11 (1995), 426–437; Lawson, Phytopathology 86 (1996), 56 suppl.), (vi) ozone resistance (Van Camp, BioTech. 12 (1994), 165–168), (v) improving the preserving of fruits (Oeller, Science 254 (1991), 437–439), (vi) improvement of starch composition and/or production (Stark, Science 242 (1992), 419; Visser, Mol. Gen. Genet. 225 (1991), 289–296), (vii) altering lipid composition (Voelker, Science 257 (1992), 72–74), (viii) production of (bio)polymers (Poirer, Science 256 (1992), 520–523), (ix) alteration of the flower color, e.g. by manipulating the anthocyanin and flavonoid biosynthetic pathway (Meyer, Nature 330 (1987), 667–678, WO90/12084), (x) resistance to bacteria, insects and fungi (Duering, Molecular Breeding 2 (1996), 297–305; Strittmatter, Bio/Technology 13 (1995), 1085–1089; Estruch, Nature Biotechnology 15 (1997), 137–141), (xi) inducing and maintaining male and/or female sterility (EP-A1 0 412 006; EP-A1 0 223 399; WO93/25695) and (xii) remediation of contaminated soils (Cunningham, TIBTECH 13 (1995), 393–397).

Furthermore, it is possible to use the nucleic acid molecules according to the invention as molecular markers in plant breeding. Moreover, the overexpression of nucleic acid molecules according to the invention may be useful for the alteration or modification of plant/pathogen interaction. The term "pathogene" includes, for example, bacteria, viruses and fungi as well as protozoa.

Furthermore, the present invention relates to the use of a regulatory sequence, a recombinant DNA molecule, a vector, a compound and/or the antibody of the invention for the expression of heterologous proteins in basal endosperm transfer layer cells, for modification of solute partitionary in the endosperm, for conferring or improving disease resistance, for the improvement of endosperm derived products or for the expression of enzymes affecting the quality of cotton fibre and aromatic oils.

Beside the above described possibilities to use the nucleic acid molecules according to the invention for the genetic engineering of plants with modified characteristics and their use to identify homologous molecules, the described nucleic acid molecules may also be used for several other applications, for example, for the identification of nucleic acid molecules which encode proteins which interact with the BETL proteins described above. This can be achieved by assays well known in the art, for example, as described in Scofield (Science 274 (1996), 2063–2065) by use of the so-called yeast "two-hybrid system". In this system the protein encoded by the nucleic acid molecules according to the invention or a smaller part thereof is linked to the DNA-binding domain of the GAL4 transcription factor. A yeast strain expressing this fusion protein and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of a protein of the invention, the complex is able to direct expression of the reporter gene. In this way the nucleic acid molecules according to the invention and the encoded peptide can be used to identify peptides and proteins interacting with BETL proteins.

Other methods for identifying compounds which interact with the proteins according to the invention or nucleic acid molecules encoding such molecules are, for example, the in vitro screening with the phage display system as well as filter binding assays or "real time" measuring of interaction using, for example, the BIAcore apparatus (Pharmacia); see references cited supra.

These and other embodiments are disclosed and encompassed by the description and examples of the present invention. For example, further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tigr.org/, are known to the person skilled in the art and can also be obtained using, e.g., http://www.lycos.com. An overview of patent information in biotechnology and a survey of relevant sources of patent information useful for retrospective searching and for current awareness is given in Berks, TIBTECH 12 (1994), 352–364.

The Figures show:

FIG. 1: Genomic DNA from maize A69Y was digested with the following enzymes, fractionated on a 0.7% agarose gel and blotted onto Hybond-N membrane for hybridization with random primer labelled insert fragments from BETL-2 to 4 clones: 1. BamH1, 2. Bgl2. 3. EcoR1, 4. Hind3, 5. Nco1, 6. Sph1.

Figure 2:
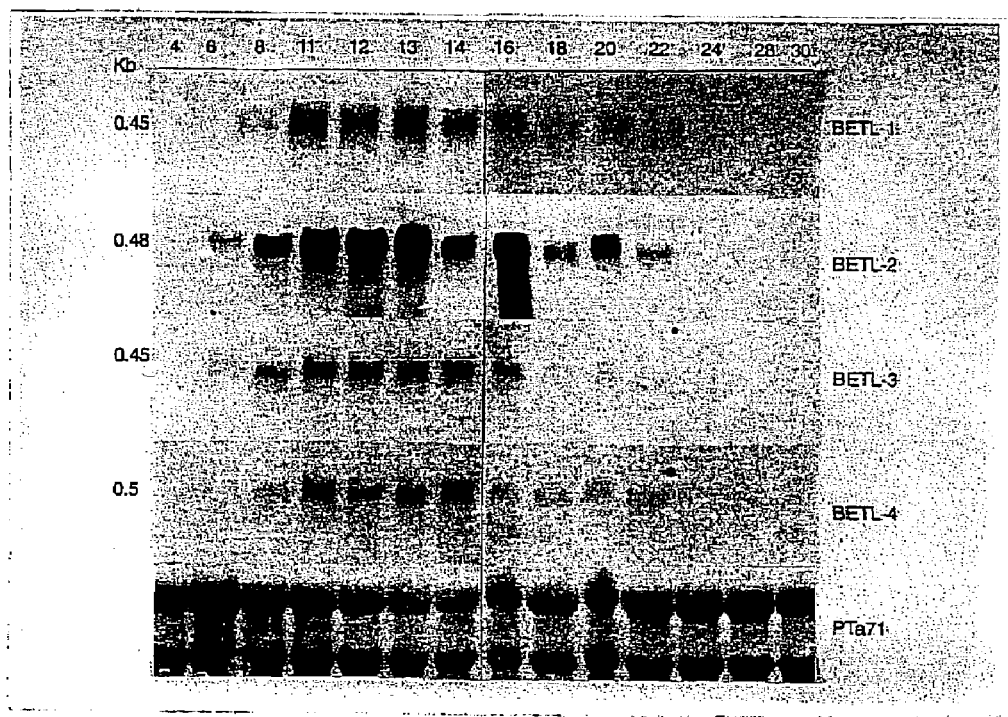

FIG. 2: Northern blot: developmental expression of BETL-1 to 4. 40 µg total RNA from kernels harvested at between 4 and 30 days after pollination (as indicated) were analysed by Northern blotting using as probes random primer labelled inserts of BETL-1 to 4 cDNA, and a ribosomal RNA probe, pTA71, as loading control.

Figure 3:
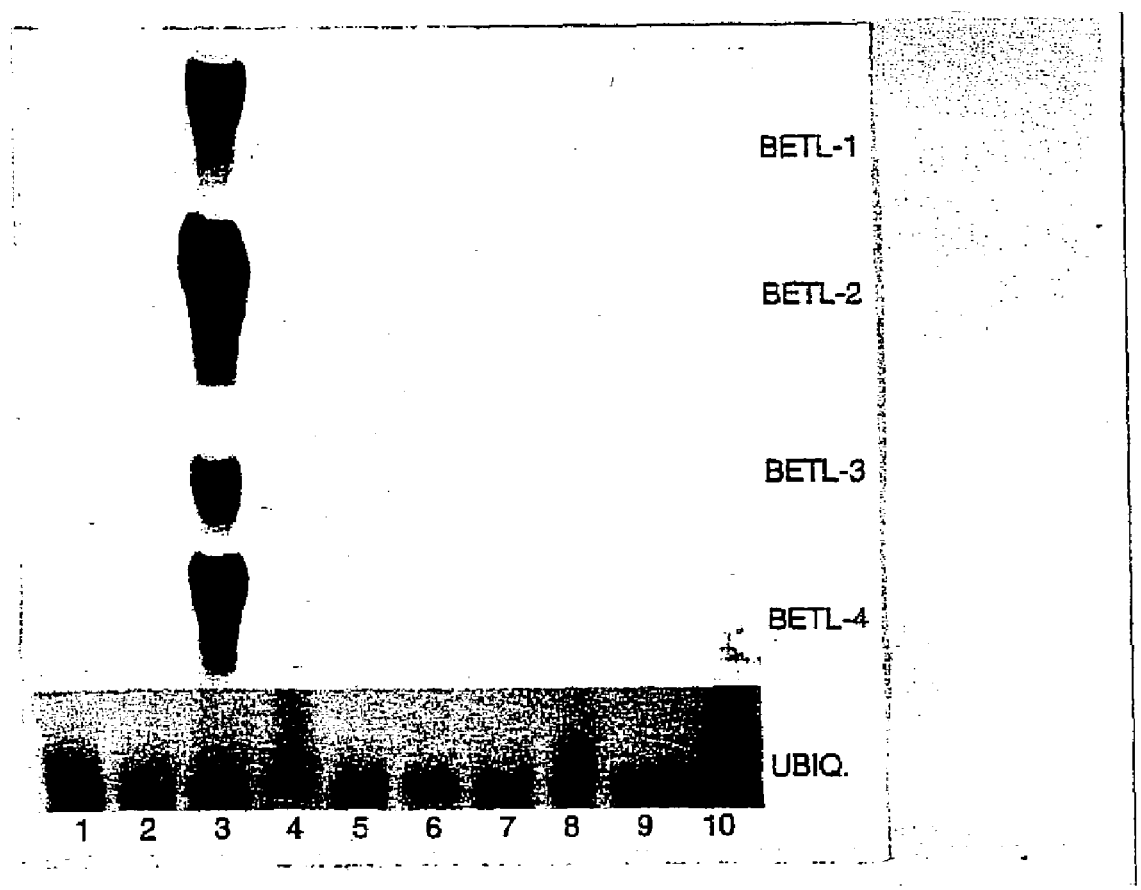

FIG. 3: Northern blot: Tissue-specificity of BETL-1 to 4. Total RNA fractionated as in FIG. 2, obtained from: 1) unfertilized caryopses, 2) endosperm top-halves 3) endosperm bottom halves, 4) leaf, 5) roots (total), 6) primary root minus tips, 7) primary root tips only, 8) silks, 9) tassel, 10) coleoptile. Ubiquitin cDNA probe as loading control.

Figure 4A:
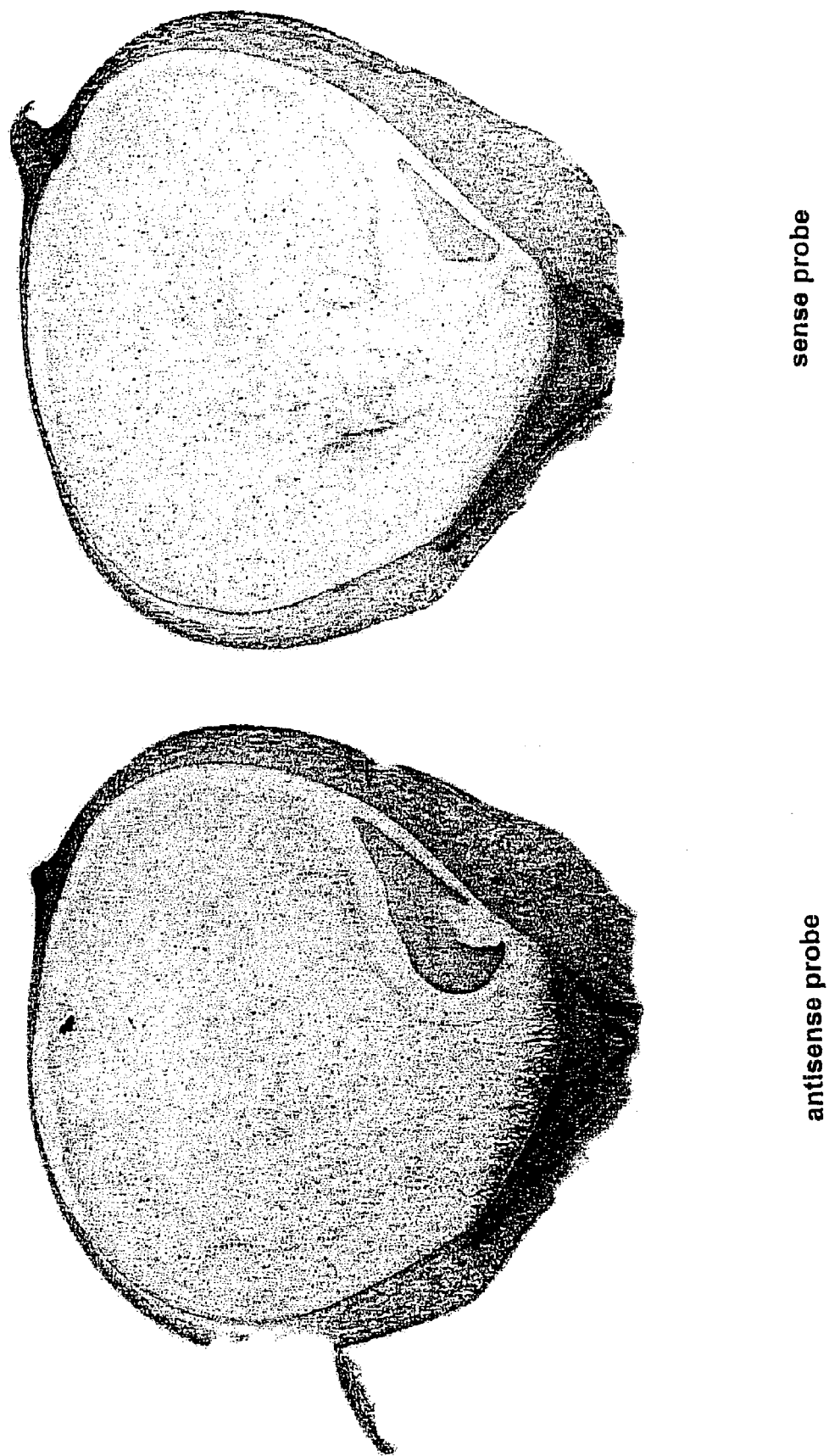
Figure 4:
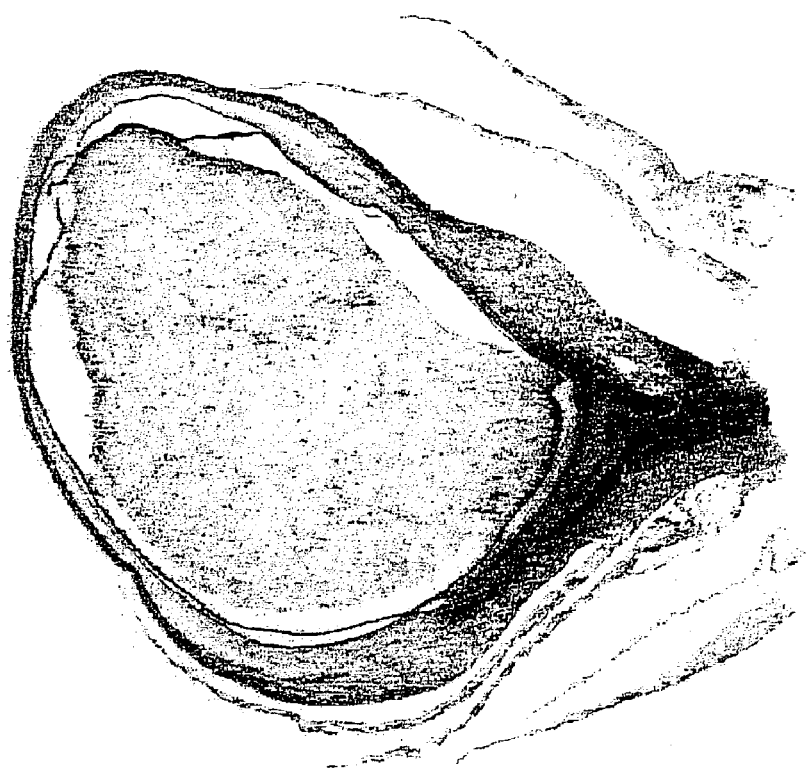
Figure 4:
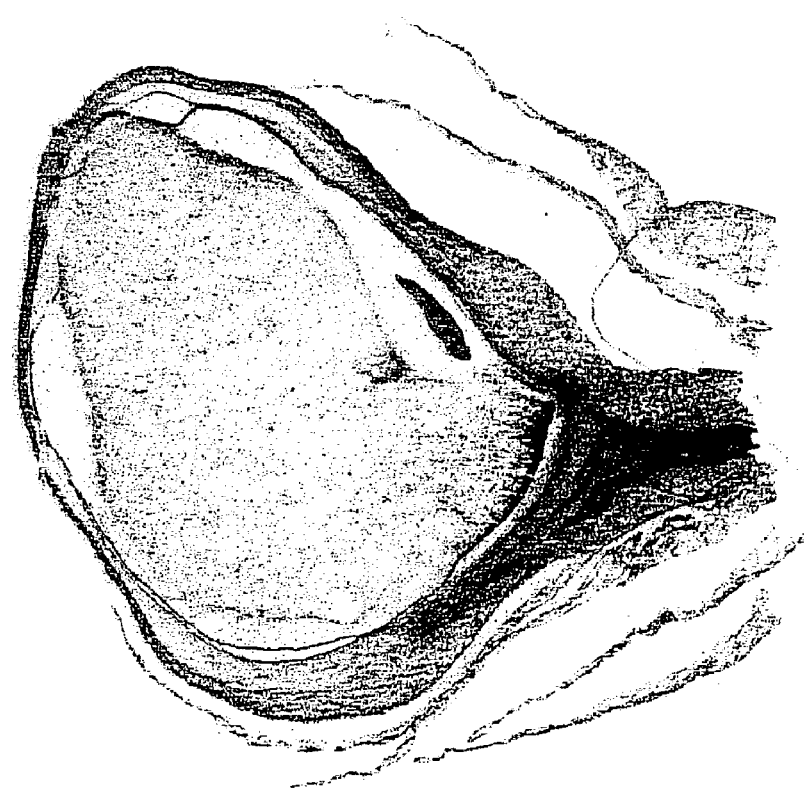

FIG. 4: in situ hybridization of BETL-2 cDNA probe to 16 d.a.p. section of maize endosperm.

Figure 5:
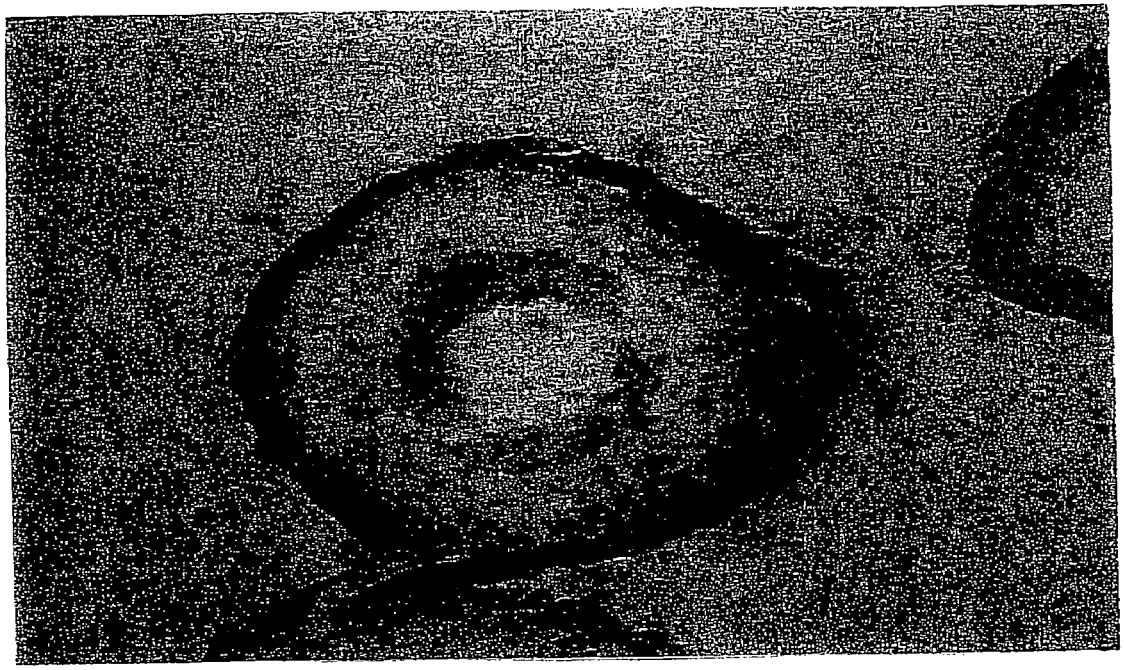

FIG. 5: BETL-2 promoter/GUS expression in transgenic tobacco. Signal in fused testa/pericarp of the developing seed at 10 d.a.p.

Figure 6:
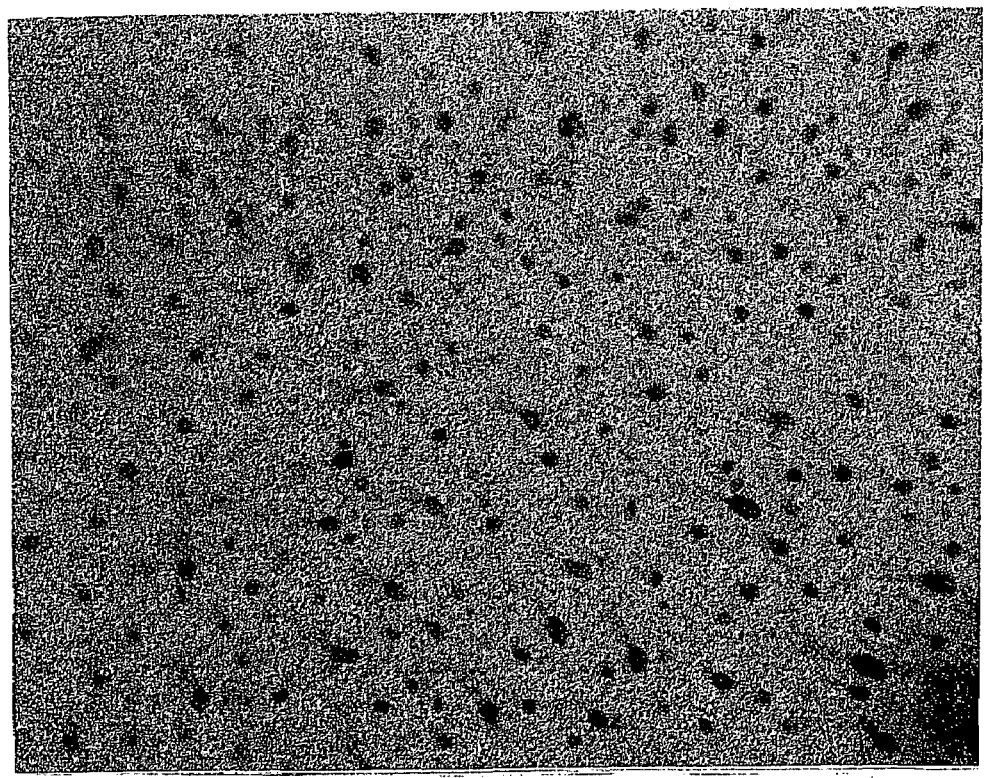

FIG. 6: BETL-2 promoter/GUS expression in transgenic tobacco. Signal in leaf hairs.

Figure 7:

FIG. 7: BETL-2 promoter/GUS expression in transgenic tobacco. Signal in leaf hairs, showing signal largely restricted to terminal gland cells.

Figure 8:
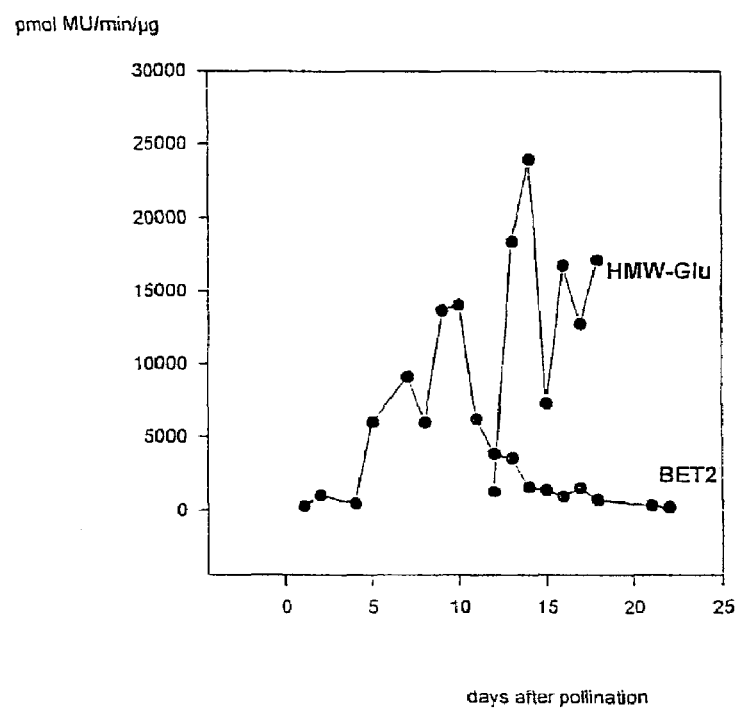

FIG. 8: BETL-2 promoter/GUS expression in transgenic tobacco seeds. Comparison of transient expression of the BETL2 promoter with the expression from HMW-Glu, a storage protein promoter.

Figure 9:

FIG. 9: BETL-2 promoter/GUS expression in transgenic Arabidopsis. Expression in stigmatic papillae.

Figure 10:
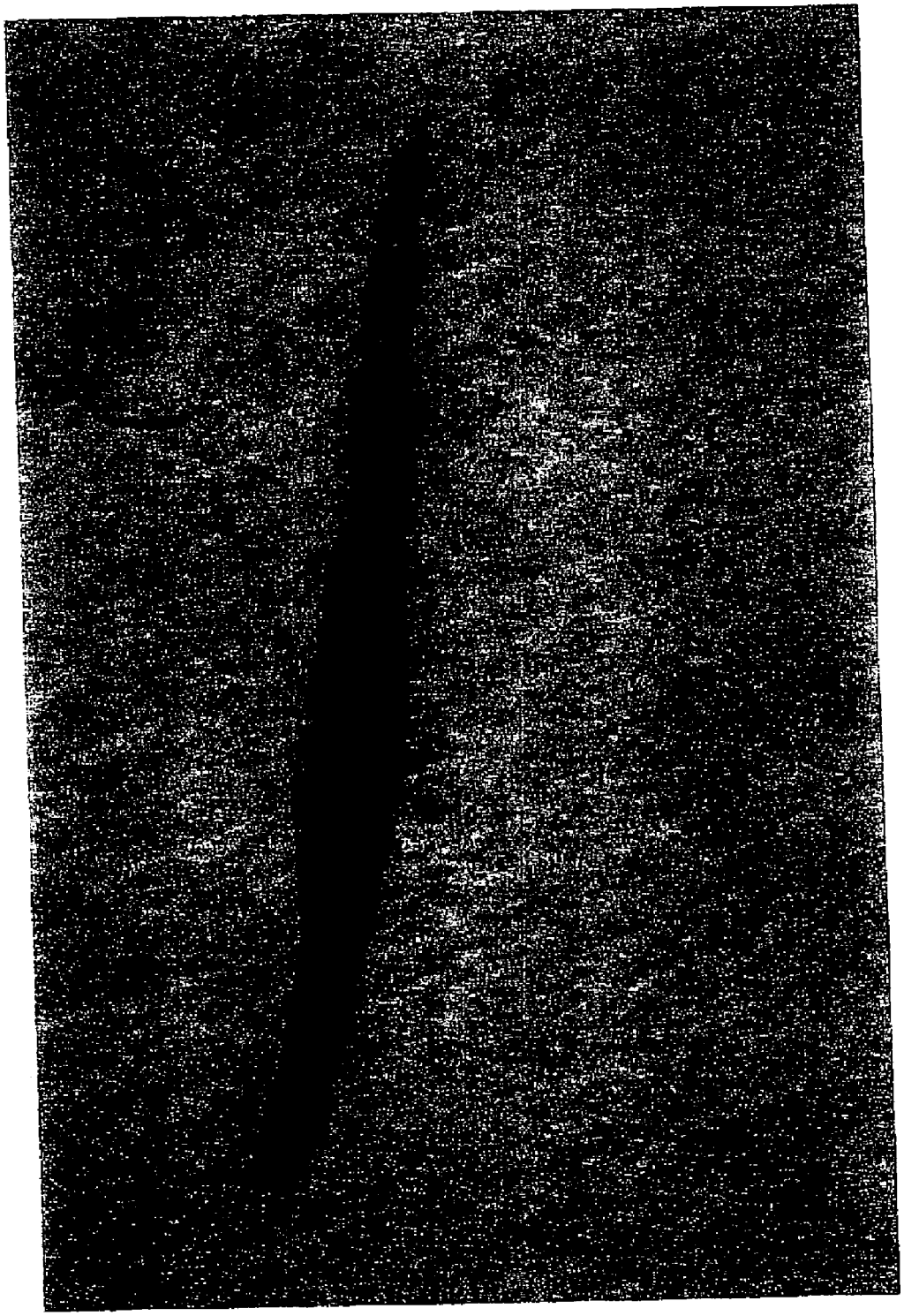

FIG. 10: BETL-2 promoter/GUS expression in transgenic Arabidopsis. Expression in developing seeds at 9 DAP.

Figure 11:
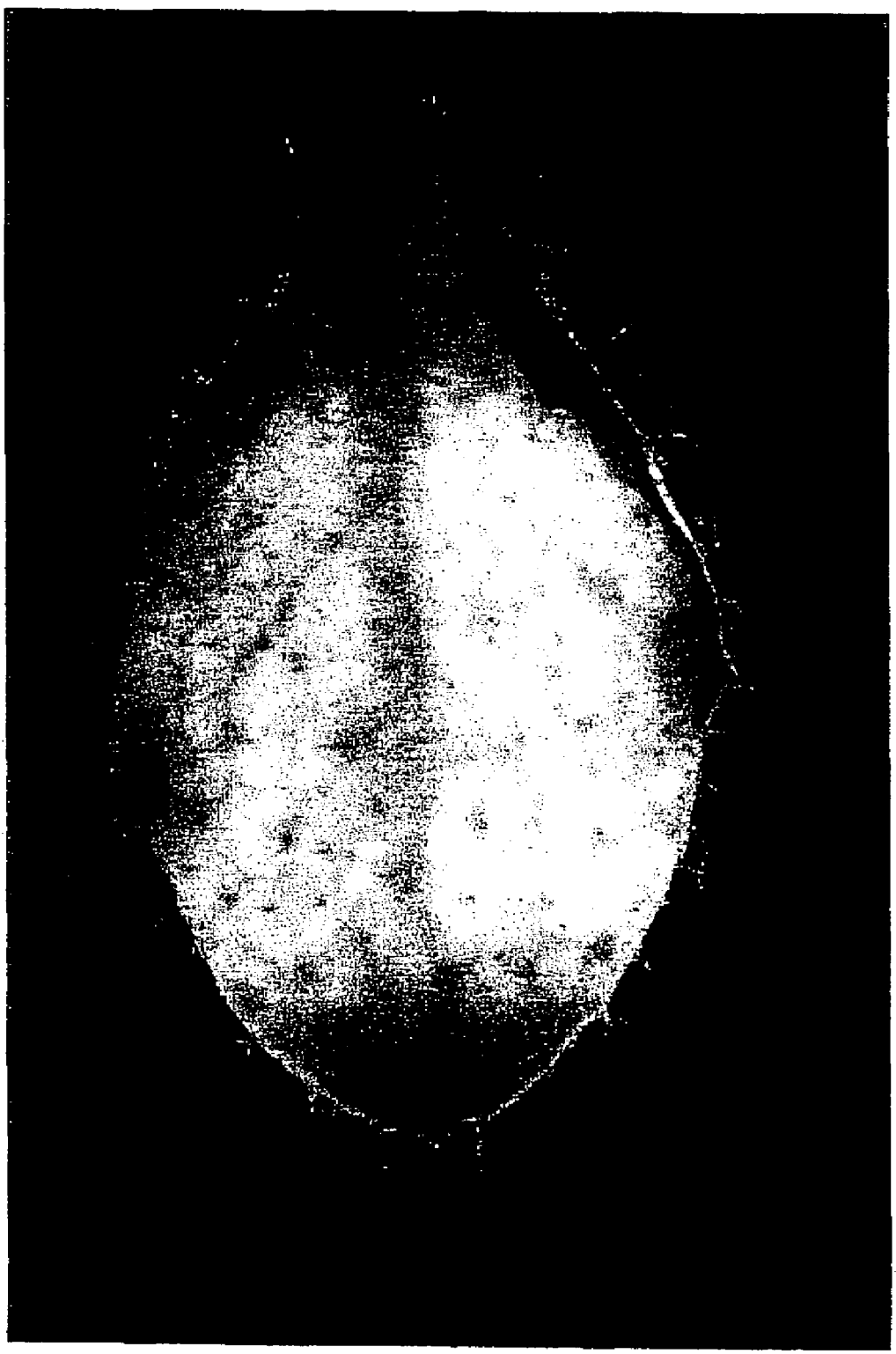

FIG. 11: BETL-2 promoter/GUS expression in transgenic Arabidopsis. Expression in hyathodes on the leaf margins.

Figure 12:
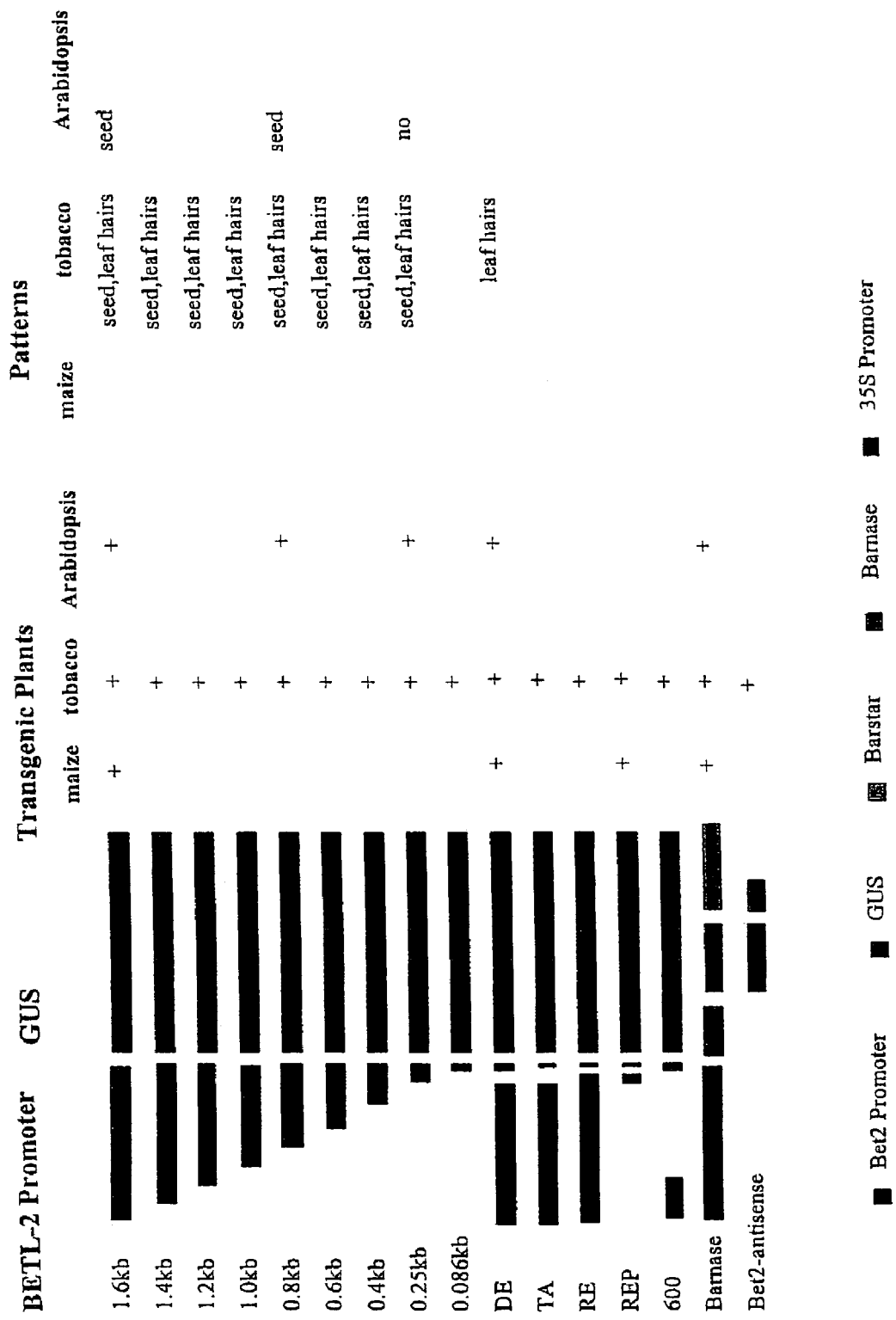

FIG. 12: BETL-2 promoter deletion analysis.

FIG. 13: Clustal comparison of BETL-1 to -4 promoter sequences.

THE EXAMPLES ILLUSTRATE THE INVENTION:

Example 1

Isolation of BETL-2 to BETL-4 cDNAs

The techniques used for cDNA isolation and characterization are as described in Maniatis et al., 1982 and Sambrook et al., 1989, unless stated otherwise. A cDNA library was prepared in lambda phagemid insertion vector ZAPII, using as a template poly(A)+ RNA purified from manually dissected endosperms harvested at 10 days after pollination (DAP). A cDNA probe prepared from 10-DAP endosperm mRNA was $^{32}$P-labelled with $\alpha^{32}$P-dCTP by reverse transcription. This probe was subtracted for maturation stage transcripts by hybridization with a 10:1 molar excess of photobiotinylated mRNA from 25-DAP endosperm. The sequences common to both mRNA populations were removed by streptavidin binding and subsequent phenol extraction. The subtraction hybridization procedure was repeated twice as described previously (Sive and St. John, 1988). The cDNA sequences contained in 500 clones from this library were amplified by PCR, and screened with cDNA probes prepared from poly(A)+ RNAs extracted from either top or bottom halves of 10 DAP seeds. 14 clones giving a strong hybridization signal with the bottom probe and a negligible signal with the top one were selected for further studies. Selected clones were used as probes in Northern hybridization experiments, and three of them were shown to hybridize exclusively to a bottom RNA sample, in filters containing RNAs from top halves of the seed as well as different maize tissues a similar result was obtained with the previously isolated BETL-1 and therefore these genes were named BETL-2, BETL-3 and BETL-4.

The new BETL genes are expressed only in the basal cells of the endosperm. The cDNA sequences of the BETL-2 to 4 genes were used to produce DIG-labeled sense and antisense RNA probes by in vitro transcription. In situ hybridizations of these probes to sagittal sections of maize kernels demonstrated that all probes were transfer cell specific. No signal was detected in embryo, seed coat, endosperm or maternal tissues. Expression of BETL1–4 genes could also be detected in developing endosperm. In situ hybridization to 8 DAP seed sections showed that the BETL mRNA accumulation in the transfer cells starts at the very early stages of cell differentiation. Hybridization of the BETL probes with filter-bound mRNA isolated from various developmental stages showed an accumulation kinetic that almost parallels that shown for BETL-1. The expression level was nevertheless quite different for the different genes, BETL-2 being the most highly expressed followed by BETL-1, BETL-4, and BETL-3 as the gene showing the lowest level of mRNA accumulation (see FIGS. 2 and 3). BETL-3 appears to be a defensin-like protein while BETL-4 shows homology with Bourmann-Birk family of α-amylase/trypsin inhibitors.

Example 2

Inverse-PCR Cloning of BETL-1 to 4 Promoters

The copy number and genomic organization of the BETL-1 (Hueros et al., 1995) and BETL-2 to 4 genes was checked by Southern hybridization (FIG. 1). The results showed the BETL-1 locus consists of three closely linked gene copies, but BETL-2 to -4 seem all to be single copy in the maize genome. In order to clone the sequences upstream of the coding regions, inverse-PCR was used. In the case of BETL-1, genomic DNA was digested with XbaI, denatured and allowed to anneal to a reverse primer derived from the cDNA sequence; after primer extension, a blunt-ended adaptor was ligated and PCR was performed using a nested reverse primer derived from the cDNA, and a forward primer derived from the adaptor sequence. The XbaL-digested I-PCR fragment (1.5 Kbp) was cloned and sequenced. The reverse primer from the cDNA sequence was designed to include the complete coding region into the final I-PCR product and therefore a 0.5 Kbp sequence comprising the coding region and a small intron was included in the clone along with 1 Kbp promoter fragment. The strategy used for the cloning of the promoter sequences of BETL-2 to 4 was slightly different. In these cases a physical map of the genomic sequences upstream the coding region was constructed by mean of genomic southern analysis. With this information, genomic DNA was digested with selected restriction enzymes, genomic fragments containing a piece of the upstream sequences and the coding sequence were gel purified and self-ligated in a large volume to favour the formation of circular molecules, that were subsequently amplified by PCR with forward and reverse primers, derived from the coding sequence. EcoR1 was the restriction enzyme used for the initial digestion of genomic DNA in the case of BETL-2, and Nco1 was used for BETL-3 These digests yielded promoter fragments of 1.6 Kbp for BETL-2 and 0.8 Kbp for BETL-3. In the case of BETL-4 the enzyme selected was Dral and the promoter isolated was 0.5 Kbp long. In detail, the procedure used was as follows:

For BETL-2 promoter isolation: 100 micrograms genomic DNA from the maize variety A69Y were digested with EcoR1. The digested DNA was electrophoresed and the restriction fragments comprising between 1.8 and 2.4 Kbp were purified from the gel. One tenth of the recovered DNA was self-ligated in a volume of 50 microlitres, EtOH precipitated and resuspended in 10 microlitres of water. One microlitre of the self-ligated DNA was used for PCR with primers forward (5'-GACCATGGCACGCACAA-CAAGTG-3'; SEQ ID NO:11) and reverse (5'-GAAGCT-GCTGCACTTCGCCATG-3'; SEQ ID NO: 12). PCR reaction was performed according to the manufacturer's description. The program for the PCR was: 94° C., 2'30" followed by 35×: 94° C., 40"; 65°0 C. 1', 72° C., 3', and finally a step a The amplified fragment of 1.9 Kbp was digested with Nco1+EcoR1, blunt ended and the remaining 1.6 Kbp fragment cloned in the EcoR5 site of Bluescript.

For BETL-3 promoter isolation the same protocol as for BETL-2 was followed, in this case the genomic DNA was digested with Nco1, the fragments ranging in size from 1.2 Kbp to 1.6 Kbp were gel purified and the primers used for I-PCR were: forward (5'-GATGCACCGTAGTGCATC-TATGC-3'; SEQ ID NO: 13) and reverse (5'-GCCATGTA-CACAATCCTCATTGTC-3'; SEQ ID NO: 14). The PCR program was also identical to that used for BETL-2 except that the annealing temperature was reduced to 55° C. and the extension time was reduced to 2'. The final PCR product was blunt ended, kinased and ligated into the EcoR5 site of Bluescript.

For BETL-4 promoter isolation the same protocol as for BETL-3 was followed, in this case the genomic DNA was digested with Dra1, the fragments ranging in size from 1 Kbp to 1.4 Kbp were gel purified and the primers used for I-PCR were: forward (5'-CAAGGCATGCATGACAACT-GTGTC-3'; SEQ ID NO: 15) and reverse (5'-CAG-GAGAAGGAGGACTATGTTGTC-3'; SEQ ID NO: 16).

Example 3

Analysis of Expression Pattern of the BETL-2 Promoter in Transgenic Tobacco and Arabidopsis Plants The BETL-2 promoter fragment was fused as a Kpn-Nco PCR product generated with specific oligos to the GUS coding region of the plasmid pRT106. The cassette was excised with HinD3 and cloned into pBIN19 for *Agrobacterium*-mediated transformation using the leaf-disc cocultivation method of *Nicotiana tabacum* cv. SR1 explants. Transgenic plants were selected on Kanamycin resistance basis, and tested for GUS expression by staining With X-Gluc. Arabidopsis transformation was carried out by the vacuum infiltration of immature inflorescences (Bechtold et al., 1993), followed by selection of kanamycin-resistant T1 progeny on agar plates. Precise localization of cells expressing GUS was carried out by embedding and sectioning immature seeds by standard techniques (Gallagher, 1992) before staining with X-Gluc under conditions minimizing diffusion of the indole product, and examining thin sections by light microscopy. Quantitative GUS assays (specific enzyme activities) on immature seeds were carried out using the fluorogenic GUS substrate Methyl Umbelliferyl Glucuronide.

Example 4

Summary of Expression Data Obtained with BETL-2 Promoters

BETL-2: A full-length promoter/GUS construct was introduced into tobacco and also series of deletions (FIG. 12) in tobacco. Pattern of expression: in aerial hair cells, just the terminal (gland) cell. Expression also in fused testa/pericarp of the developing seed from 1–2 days after pollination, peaking at ca. 10 DAP and declining to zero by ca. 18 DAP. As shown in FIG. 12, seed and leaf hair-specific expression can be conferred by a promoter fragment of 250 bp, but only the leaf hair activity is retained in an 86 bp promoter fragment. In Arabidopsis, seedcoat expression was observed with the full length promoter and a fragment of 800 bp, but not with the 250 bp deletion.

A full-length promoter/GUS construct was also introduced into Arabidopsis. Pattern of expression: hyathodes on true leaves, stigmatic papillar cells, seed coat (transiently expressed as for tobacco). Weaker expression in developing embryo.

REFERENCES

Bechtold, Comptes Rendus de L'Academie des Sciences Serie III Sciences de la Vie 316 (10) (1993), 1194–1199
Bureau, Plant Cell 4 (1992), 1283–1284
Charlton, Endosperm development in Zea mays;
Chen, Proc. Natt. Acad. Sci. 94 (1997), 3431–3435
Colot, Embo J 12 (1987), 3559–3564
Doan, Plant Mol. Biol. 31 (1996), 877–886
Epplen, FEBS Letters 389 (1996), 92–95
Forde, Nucl. Acids. Res. 13 (1985), 7327–7339
Frias, The Plant Cell 8 (1996), 1533–1544
Giovinazzo, Plant. Mol. Biol. 19 (1992), 257–263
Gallagher, GUS Protocols. San Diego, Academic Press (1992)
Hamada, Mollecular and Cellular Biology 4 (1984), 2622–2630

Hammond-Kosack, Embo J 12 (1993), 545–554
Hueros,G., Plant Cell 7 (1995), 747–757
Kalla, The Plant Journal 6 (1996), 849–860
Kaukinen, Nucleic Acid Research 20, 2955–2958
Maniatis, Molecular Cloning: A Laboratory Manual, Cold Spring Harbor, N.Y.: Cold Spring Harbor Press (1982)
Matzke, Plant. Mol. Biol. 14 (1990), 323–332
McElroy, Trends Biotechnol. 12 (1994), 62–68
Montag, Maydica 41 (1996), 241–254
Müller, The Plant Journal 4 (1995), 343–355
Nadir, Proc. Natl. Acad. Sci. 93 (1996) 6470–6475
Ohno, Springer-Verlag (1970)
Pate, Annu. Rev. Plant Physio. 23 (1972), 173–196
Rio, Plant Molecular Biology 32 (1996), 1221–1226
Robert, The Plant Cell 1 (1989), 569–578
Rosales, Embo J 6 (1987), 3015–3025
Roussell, Mol. Gen. Genet. 211 (1988), 202–209
Sambrook, Molecular Cloning: A Laboratory Manual. 2nd ed., Cold Spring Harbour Laboratory Press, Cold Spring Harbour/N.Y. (1989)
SanMiguel, Sience 274 (1988), 765–768
Shannon, New York: Alan Liss Inc., 265–277
Sive, Nucl. Acids Res. 16 (1988), 10937
Thomas, Plant Cell 2 (1990), 1171–1180
Thompson, Plant Mol. Biol. 15 (1990), 755–764
Wessler, Curr Opin Genet Devel 5 (1995), 814–821
Yougn-Kwan, The Plant Cell 6 (1994), 1177–1186

The invention claimed is:

1. An isolated nucleic acid molecule which confers expression of a heterologous DNA sequence in basal endosperm transfer layer cells, wherein said isolated nucleic acid molecule comprises
   (a) the DNA sequence set forth in SEQ ID NO:8 or
   (b) nucleotides 1350 to 1615 of the nucleotide sequence set forth in SEQ ID NO:8.

2. A recombinant DNA molecule comprising the isolated nucleic acid molecule as set forth in claim 1.

3. The recombinant DNA molecule of claim 2, wherein said isolated nucleic acid molecule is operably linked to a heterologous DNA sequence.

4. The recombinant DNA molecule of claim 3, wherein said heterologous DNA sequence encodes a peptide, protein, antisense RNA, sense RNA and/or ribozyme.

5. A vector comprising the isolated nucleic acid molecule of claim 1 or the recombinant DNA molecule of claim 3.

6. The vector of claim 5, which further comprises a selection marker.

7. An isolated cell transformed with the isolated nucleic acid molecule of claim 1.

8. A method for the production of transgenic plants, plant cells or plant tissue comprising introducing the isolated nucleic acid molecule of claim 1 or the recombinant DNA molecule of claim 3 into the genome of said plants, plant cells or plant tissue.

9. A transgenic plant cell which contains stably integrated into its genome the recombinant DNA molecule of claim 3.

10. A transgenic plant or transgenic plant tissue comprising the plant cell of claim 9.

11. Harvestable parts or propagation material of a plant comprising the plant cell of claim 9, wherein said harvestable parts or propagation material comprises the transgenic plant cell.

12. A method of expressing a heterologous DNA sequence in basal endosperm transfer layer cells, for modification of solute partitionary in the endosperm, for conferring or improving disease resistance, for the improvement of endosperm products or for the expression of enzymes affecting the quality of cotton fiber and aromatic oils, the method comprising:
 introducing the recombinant DNA molecule of claim 3 into the genome of a plant, plant cell or plant tissue and expressing said heterologous DNA sequence.

13. A method for the production of transgenic plants, plant cells or plant tissue comprising introducing the vector according to claim 5 into the genome of said plants, plant cells or plant tissue.

14. A transgenic plant cell which contains the vector according to claim 5, whereby said vector is stably integrated into the plant genome of said plant cell.

15. A transgenic plant or plant tissue comprising the plant cell of claim 14.

16. A transgenic plant or plant tissue comprising the vector of claim 5.

17. The transgenic plant or transgenic plant tissue of claim 10, wherein the plant or plant tissue is maize.

18. A plant transformed with the isolated nucleic acid molecule of claim 1.

19. A plant transformed with the recombinant DNA molecule of claim 3.

* * * * *

SEQUENCE LISTING

```
<160> NUMBER OF SEQ ID NOS: 16

<210> SEQ ID NO 1
<211> LENGTH: 379
<212> TYPE: DNA
<213> ORGANISM: Zea mays
<220> FEATURE:
<221> NAME/KEY: CDS
<222> LOCATION: (44)..(328)

<400> SEQUENCE: 1
ggcacgagta ttagactatt gtagctcata tcatctgtca ccc atg gcg aag tgc        55
                                             Met Ala Lys Cys
                                               1 agc agc ttc caa gga tta ttc tgg ttg ctt tcc atg att ctt cta gca       103
Ser Ser Phe Gln Gly Leu Phe Trp Leu Leu Ser Met Ile Leu Leu Ala
  5              10                  15                  20 tcc ttt gtt gct cat gca cgc aca aca agt ggg caa acc aaa gag gac       151
Ser Phe Val Ala His Ala Arg Thr Thr Ser Gly Gln Thr Lys Glu Asp
             25                  30                  35 agc aat gct agg aac atg acg atg acc aag acg agg gca tca ggc aac       199
Ser Asn Ala Arg Asn Met Thr Met Thr Lys Thr Arg Ala Ser Gly Asn
         40                  45                  50 ata ctt gtt agc cgt aat gac gac ggg cca tgc tat cta gat tcc ggt       247
Ile Leu Val Ser Arg Asn Asp Asp Gly Pro Cys Tyr Leu Asp Ser Gly
     55                  60                  65 ctt aat gag tac gtc tgc aga aag act aat aag tgc tat aag agc ttg       295
Leu Asn Glu Tyr Val Cys Arg Lys Thr Asn Lys Cys Tyr Lys Ser Leu
 70                  75                  80 gtg ctc tgc gtg gcg agt tgt caa cca tca tca tgaattcatg atactgcgga     348
Val Leu Cys Val Ala Ser Cys Gln Pro Ser Ser
 85                  90                  95 gacatcatga tactgcggag acagacggcg a                                    379

<210> SEQ ID NO 2
<211> LENGTH: 95
<212> TYPE: PRT
<213> ORGANISM: Zea mays

<400> SEQUENCE: 2

Met Ala Lys Cys Ser Ser Phe Gln Gly Leu Phe Trp Leu Leu Ser Met
  1               5                  10                  15

Ile Leu Leu Ala Ser Phe Val Ala His Ala Arg Thr Thr Ser Gly Gln
                 20                  25                  30

Thr Lys Glu Asp Ser Asn Ala Arg Asn Met Thr Met Thr Lys Thr Arg
```

```
                  35                  40                  45
Ala Ser Gly Asn Ile Leu Val Ser Arg Asn Asp Asp Gly Pro Cys Tyr
 50                  55                  60

Leu Asp Ser Gly Leu Asn Glu Tyr Val Cys Arg Lys Thr Asn Lys Cys
 65                  70                  75                  80

Tyr Lys Ser Leu Val Leu Cys Val Ala Ser Cys Gln Pro Ser Ser
                 85                  90                  95

<210> SEQ ID NO 3
<211> LENGTH: 406
<212> TYPE: DNA
<213> ORGANISM: Zea mays
<220> FEATURE:
<221> NAME/KEY: CDS
<222> LOCATION: (50)..(292)

<400> SEQUENCE: 3
cctgcatata ctaacactgc aaaactgaaa aggtgatag caaacgaca atg agg att      58
                                                     Met Arg Ile
                                                      1 gtg tac atg gca gct gtt atg tgt ttg gtt ctt gca aca atg tct tct     106
Val Tyr Met Ala Ala Val Met Cys Leu Val Leu Ala Thr Met Ser Ser
      5                  10                  15 acc tcc cca tca ttc tgc caa gct ggg ggc tgc atc ggc tgc cca cgg     154
Thr Ser Pro Ser Phe Cys Gln Ala Gly Gly Cys Ile Gly Cys Pro Arg
 20                  25                  30                  35 gcc cca cca ccg ccg tcc gat gag aca tgc tac gag gac ctg aag tgt     202
Ala Pro Pro Pro Pro Ser Asp Glu Thr Cys Tyr Glu Asp Leu Lys Cys
                 40                  45                  50 tcg gct tcg agg tgc cac ctg ggt tgc ata cac agg ggc tac aag ggt     250
Ser Ala Ser Arg Cys His Leu Gly Cys Ile His Arg Gly Tyr Lys Gly
                     55                  60                  65 acg ggt tcg tac tgc cgt ggg agg gac tgc tgc tgc aaa cat               292
Thr Gly Ser Tyr Cys Arg Gly Arg Asp Cys Cys Cys Lys His
         70                  75                  80 tgatgcaccg tagtgcatct atgcatttca tggcctggcc atacaataaa cctagatgtg     352
tatcctttgc ctccgacgac tataaatgaa atgaaatact actaaggttc aaaa            406

<210> SEQ ID NO 4
<211> LENGTH: 81
<212> TYPE: PRT
<213> ORGANISM: Zea mays

<400> SEQUENCE: 4

Met Arg Ile Val Tyr Met Ala Ala Val Met Cys Leu Val Leu Ala Thr
 1               5                  10                  15

Met Ser Ser Thr Ser Pro Ser Phe Cys Gln Ala Gly Gly Cys Ile Gly
                 20                  25                  30

Cys Pro Arg Ala Pro Pro Pro Ser Asp Glu Thr Cys Tyr Glu Asp
             35                  40                  45

Leu Lys Cys Ser Ala Ser Arg Cys His Leu Gly Cys Ile His Arg Gly
 50                  55                  60

Tyr Lys Gly Thr Gly Ser Tyr Cys Arg Gly Arg Asp Cys Cys Cys Lys
 65                  70                  75                  80

His

<210> SEQ ID NO 5
<211> LENGTH: 496
<212> TYPE: DNA
```

<213> ORGANISM: Zea mays
<220> FEATURE:
<221> NAME/KEY: CDS
<222> LOCATION: (22)..(345)

<400> SEQUENCE: 5

```
ggcacgagca cgcgttcaaa g atg cgt ggg gaa gac aac ata gtc ctc ctt        51
                        Met Arg Gly Glu Asp Asn Ile Val Leu Leu
                         1               5                  10 ctc ctg ctc ctg ttt gct gta att tcc ccg aac caa gtg att ggt agt        99
Leu Leu Leu Leu Phe Ala Val Ile Ser Pro Asn Gln Val Ile Gly Ser
             15                  20                  25 gct tgt act ccg gaa cag aag gct gcc atc cta aac caa tgc gaa gag       147
Ala Cys Thr Pro Glu Gln Lys Ala Ala Ile Leu Asn Gln Cys Glu Glu
                 30                  35                  40 tac atc aag cct gga tac ccc ctt ata ctg cca tcg tac gcc agt gtg       195
Tyr Ile Lys Pro Gly Tyr Pro Leu Ile Leu Pro Ser Tyr Ala Ser Val
             45                  50                  55 tgt tgc gag aag gtg aga gat gtg cca aat agg gac atg aac tgc atc       243
Cys Cys Glu Lys Val Arg Asp Val Pro Asn Arg Asp Met Asn Cys Ile
 60                  65                  70 gtt gat ctg ctc acg cct cca gag aag gcg aaa cac ggt gtc gac aag       291
Val Asp Leu Leu Thr Pro Pro Glu Lys Ala Lys His Gly Val Asp Lys
 75                  80                  85                  90 ata aaa cgt ctg aaa gat ctc tgc gac aac tcg cct cat cat cag gtg       339
Ile Lys Arg Leu Lys Asp Leu Cys Asp Asn Ser Pro His His Gln Val
                 95                 100                 105 gtg gtg tagacagaca gcagctgtca ttgctaatgg agttcggagg caagatatat       395
Val Val ggtctagtaa ataaagtcgt cgatcaaggc atgcatgaca actgtgtcat atgtatcttt       455
gattaagtaa agtatcactc aagatttcca gtttcttttt t                           496
```

<210> SEQ ID NO 6
<211> LENGTH: 108
<212> TYPE: PRT
<213> ORGANISM: Zea mays

<400> SEQUENCE: 6

```
Met Arg Gly Glu Asp Asn Ile Val Leu Leu Leu Leu Leu Leu Phe Ala
 1               5                  10                  15

Val Ile Ser Pro Asn Gln Val Ile Gly Ser Ala Cys Thr Pro Glu Gln
             20                  25                  30

Lys Ala Ala Ile Leu Asn Gln Cys Glu Glu Tyr Ile Lys Pro Gly Tyr
         35                  40                  45

Pro Leu Ile Leu Pro Ser Tyr Ala Ser Val Cys Cys Glu Lys Val Arg
     50                  55                  60

Asp Val Pro Asn Arg Asp Met Asn Cys Ile Val Asp Leu Leu Thr Pro
 65                  70                  75                  80

Pro Glu Lys Ala Lys His Gly Val Asp Ile Lys Arg Leu Lys Asp
             85                  90                  95

Leu Cys Asp Asn Ser Pro His His Gln Val Val Val
                100                 105
```

<210> SEQ ID NO 7
<211> LENGTH: 1038
<212> TYPE: DNA
<213> ORGANISM: Zea mays

<400> SEQUENCE: 7

-continued

```
caccaggatc aggaaccagg aatctgatac caattgtaat agaaccatgg aacaggtaac      60
agagccgatg aacacaaaga catgatttgg atcacgagca cggctcctgg taccctccac     120
ctctcacgaa gtatcaaatt atcactggaa ttcatgattc aggttacaga ggaagagccc     180 tcccttccg aacgcagtcg gcctcaactt atgccccaag ccgcccttgg cgattcataa      240
agtccttttc tttataccac atgccaaaac aaaagaaaa cactaaaaca ctcattgggt      300
ccaatctggc ccatggacgc gagagttggg cttcacttga catcgaaccc tcctagtagc     360
catggttcct tcccgccttc tgttgatttc cttcggtgtc atcacacatc gttggaccac     420
attccagacg tccatacacc gagtatacag gaaagagaga caacggggtg aaccgttgac     480
acggcctgga aacaatggtg gcggctggaa acaacagcag cgattgtgac aacgactaaa     540
tagggttgaa ccgcctttgc caatgatttt tttgccgttt accctttgcc gggtgtgaca     600
ctctgcaaaa ggtttactgt gtgtatttct ggctttgccg agtgcatggg gcactcggca     660
aagcatgtga ctctggtagt gtctatgcta tgtagacgca cctccaagct taggtatgtt     720
tcgtctaagc atttatggat aatgtctaa tatcttctta ttagattgca aaataattag      780
tagtggaaga acaaccattg caaatatgtt ggttgtcttt gtatgactaa accaatatca     840
tcatattata tcaacaacaa catatcccaa tatctatatc cataactata tctatatgta     900
aaatttctat atctctatct ctatctatat ctataactag atcttctggc acaaatgaga     960
tgtgctagag atggattcgt cttctatata agtacaagtg agatcaaaga cggagattag    1020
aacaaacaaa tcatataa                                                   1038
```

<210> SEQ ID NO 8
<211> LENGTH: 1615
<212> TYPE: DNA
<213> ORGANISM: Zea mays

<400> SEQUENCE: 8

```
actgaattcc catttgttac cgatgcctgt tactagtttc atatgatgga aaactaggag      60
caacagactt ctccaacgta cgtgttaatt ttctaattga ttcttctaac cctccaattt     120
gttgtttcat ttgattctga tgatgatcta catactgttt aatagattgg atgtcgtcgg     180
gtgtacttac gttagggact tgaagcggag atagaagaga tgtgatgttg gtctctccat     240
gtttgacaac tttctggtgg tgatccaccg tgtattgtga taagaatttc tcctttgctt     300
gacacatgta gtcctcgtat tgctgttgct catcggccgt tagtctttca acagccggct     360
tcaggatatt gtccggggga gatatcagtg tgatctttag aaccgggcca tttgaggggc     420
ctgattttta gtagatcaag acacctgtcc cagcggagtc gccaaaaaga gtgttggcgc     480
cggttcgggc accaatcact gcattgagaa cctgcgcgg tgctctctgc acaggcgcgg     540
acggttcacg gctagaggcc agacggtccg cgacctggtg cagggctcga gttccctgcc     600
taacgagacg atggtccgc gcctagggc cggacggtac gcgcgtgcac aggggcggcg      660
gagtttgtcg gcggcgtctg aatctcgctc tggggaggga ccccgccagg aaagagagat     720
cctaggcttc gtctagggtc ggcaggccac cctagacacc tctaatcaac gtagagccga     780
agagaagcga agaatttggg ggtagggaaa ggctaatcta gagctaaact agaactactc     840
ctaatgcata agtaaaacga gaatagaca cgatttgatc gattgttggg ggttcaatcg      900
gccgtagccc ttcatctata taaggggga ggtctggatc cgctacaagt tgtttcccga     960
gctaatcccg taattttagg taacaaatcc cgcgagaaac tcggaacctt aactgactct    1020
agccgacgta aattatcgaa tttccttgta gtatctgtcc ctaagaatga aaatacccttt   1080
```

```
ataagatggc aaggaccaac attgttctag aaaagaaaaa tcaggaaaag agagggcatt    1140
gtattgcccg cgggaacatg caaccgaggt aatgatattc atgaggtgtt tggttccatt    1200
gaactaaagt ttagtctgtg tcacttcgga tgttccaatg ataattgtga gtgttaaata    1260
tagtttaaat ataaaaacta attatacaga taagactaaa ggcgagacaa ttttattaaa    1320
cctaattagt ttgtatttaa ttctcatagt tgatataact agataggtag gcacatatat    1380
agagagatag atataaatag atataaataa gtagatagat agatagatag atagatagat    1440
agatagatag atagatagag atagatagat agatggactg gtagatagat taagagacat    1500
ggagatagat agacacggat agatgtttag tatataaagc aggcgtggtg atatcaaaca    1560
catcaacaca ttttggtat tagactattg tagctcatat catctgtcac ccatg         1615

<210> SEQ ID NO 9
<211> LENGTH: 809
<212> TYPE: DNA
<213> ORGANISM: Zea mays

<400> SEQUENCE: 9
ccatggaaag tatttgacaa tatttatgat tagagatatt tgctccttaa taattgcgtg     60
ggaatcgacg tatggccatg aactcaaggt atgtacaatc ctgagactcc cgttcagttt    120
tcaaaaatac aataaacggt taagagactg catatacaac cctgagattc tggatcataa    180
atgtaactaa gagacaacat gtatggagag tcgtgaagaa acgtgctatt cgcgaagaac    240
ccgtcgcttg tatttttttc acctagcctc ttagagaccc atagagaaac cctatattac    300 ataggggttgt acatgcccga atacattcca atgttacaaa ttaatgttcg tatttaccat    360
taagcaagta tatacttaag cactaaatca ttgtgcaatt actttgaata ctaatatcta    420
ttaaatctgt atctggattt agttgtttag ataccatcga aattaatagg gttgttcata    480
atgtatttga attaaaaaac aatagctatt tcgtgccata attaaattgt ttgatacgga    540
tgatatcaac aaagatctag atagaaggtt gggatatttt tcacaactgc aaaatcattt    600
cacagcagaa tatcttcgca ttattataag acgagaacat attttttgtag aagattggac    660 gatatcgaaa cttcatctcg agatatcaag caattaatgt aggacacata caatagattt    720
gcctaaccat ccccttgtat cagtccatcc atctataaat atatatctgc acacaccacc    780
acagcaggtt gataaaagca cctcatccc                                       809

<210> SEQ ID NO 10
<211> LENGTH: 539
<212> TYPE: DNA
<213> ORGANISM: Zea mays

<400> SEQUENCE: 10
tttaaaaaaa acgaatctgg ttgaagagct cgattttaat taaaaagaag aataagcttt     60
gttaaaacag acttcaagac ctaataataa acacaagaag aagttacatg catacaagag    120
aagggcatag gcacaagaaa aaactaccta gaaaggtata ggctgatcac acatgttcat    180
ttgaggcttg ggctctggtt tcgtagctat gcctttgtat ggattagtga tctacttgtc    240
tataatgact ttgtagatat taagatgcgc atggtgtaca cgcatgcttt aatgaggtg     300 attttataga tacctgcacc taatgagcat atctgagaaa gatgttcatc ataaatgtta    360
ccatatcttc acccccccccc acacacacac acacacacac gcatatccat atcgctgtat    420
tatgcatgga ggatcgcagg cattaattaa actctggagt cctttgtgact tccccttccc    480
```

```
tataaattcc actacgtatg ctcgaactgc aatagaaca tcaagtttag attcttgtt      539

<210> SEQ ID NO 11
<211> LENGTH: 23
<212> TYPE: DNA
<213> ORGANISM: Zea mays

<400> SEQUENCE: 11
gaccatggca cgcacaacaa gtg                                             23

<210> SEQ ID NO 12
<211> LENGTH: 22
<212> TYPE: DNA
<213> ORGANISM: Zea mays

<400> SEQUENCE: 12
gaagctgctg cacttcgcca tg                                              22

<210> SEQ ID NO 13
<211> LENGTH: 23
<212> TYPE: DNA
<213> ORGANISM: Zea mays

<400> SEQUENCE: 13
gatgcaccgt agtgcatcta tgc                                             23

<210> SEQ ID NO 14
<211> LENGTH: 24
<212> TYPE: DNA
<213> ORGANISM: Zea mays

<400> SEQUENCE: 14
gccatgtaca caatcctcat tgtc                                            24

<210> SEQ ID NO 15
<211> LENGTH: 24
<212> TYPE: DNA
<213> ORGANISM: Zea mays

<400> SEQUENCE: 15
caaggcatgc atgacaactg tgtc                                            24

<210> SEQ ID NO 16
<211> LENGTH: 24
<212> TYPE: DNA
<213> ORGANISM: Zea mays

<400> SEQUENCE: 16
caggagaagg aggactatgt tgtc                                            24
```